(12) United States Patent
Haight et al.

(10) Patent No.: US 11,357,644 B2
(45) Date of Patent: *Jun. 14, 2022

(54) KNEE BALANCING DEVICES, SYSTEMS AND METHODS

(71) Applicant: Synvasive Technology, Inc., El Dorado Hills, CA (US)

(72) Inventors: Michael Haight, Sacramento, CA (US); Kenneth D. Johannaber, Reno, NV (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 1277 days.

This patent is subject to a terminal disclaimer.

(21) Appl. No.: 15/784,609

(22) Filed: Oct. 16, 2017

(65) Prior Publication Data

US 2018/0049895 A1 Feb. 22, 2018

Related U.S. Application Data

(63) Continuation of application No. 13/659,280, filed on Oct. 24, 2012, now Pat. No. 9,808,356.

(Continued)

(51) Int. Cl.
*A61F 2/46* (2006.01)
*A61B 17/02* (2006.01)

(52) U.S. Cl.
CPC .......... *A61F 2/4657* (2013.01); *A61B 17/025* (2013.01); *A61B 2017/0268* (2013.01);
(Continued)

(58) Field of Classification Search
CPC ................. A61F 2/4657; A61B 17/025; A61B 2017/0268
See application file for complete search history.

(56) References Cited

U.S. PATENT DOCUMENTS 1,179,910 A 4/1916 Edwin
1,201,467 A 10/1916 Emil
(Continued)

FOREIGN PATENT DOCUMENTS

CA 2870063 A1 5/2011
CA 2842357 A1 1/2013
(Continued)

OTHER PUBLICATIONS

U.S. Appl. No. 13/659,280, filed Oct. 24, 2012, Knee Balancing Devices, Systems and Methods.
(Continued)

*Primary Examiner* — Allen Porter
*Assistant Examiner* — Yasmeen S Warsi
(74) *Attorney, Agent, or Firm* — Schwegman Lundberg & Woessner, P.A.

(57) ABSTRACT

Devices, systems and methods are provided for facilitating knee balancing during a knee replacement surgery. A system can include a force sensor, a main body, a moveable sensor platform, and an adjustment mechanism. The force sensor can sense one or more forces applied within a knee joint, including forces applied on a medial side and a lateral side. The movable sensor platform can be coupled between the force sensor and the main body. The adjustment mechanism can adjust the moveable sensor platform, relative to the main body, thereby adjusting a collective height of the system. A method can include inserting portions of a knee balancing system into a gap formed between a cut distal end of a femur and a cut proximal end of a tibia, adjusting an adjustable mechanism of the system to increase or decrease a collective system height, and sensing and displaying the medial and lateral forces.

20 Claims, 18 Drawing Sheets

Related U.S. Application Data

(60) Provisional application No. 61/550,766, filed on Oct. 24, 2011.

(52) U.S. Cl.
CPC ............... *A61F 2002/4658* (2013.01); *A61F 2002/4661* (2013.01); *A61F 2002/4666* (2013.01)

(56) References Cited

U.S. PATENT DOCUMENTS

| | | |
|---|---|---|
| 1,726,241 A | 8/1929 | Theodore |
| 2,702,550 A | 2/1955 | Rowe |
| 2,854,981 A | 10/1958 | Marshal |
| 3,554,197 A | 1/1971 | Arthur |
| 3,678,934 A | 7/1972 | Warfield et al. |
| 3,978,862 A | 9/1976 | Morrison |
| 4,153,742 A | 5/1979 | Boehn et al. |
| 4,211,228 A | 7/1980 | Cloutier |
| 4,220,146 A | 9/1980 | Cloutier |
| 4,501,266 A | 2/1985 | McDaniel |
| 4,524,766 A | 6/1985 | Petersen |
| 4,567,798 A | 2/1986 | Brdicko |
| 4,567,886 A | 2/1986 | Petersen |
| 4,584,999 A | 4/1986 | Arnegger |
| 4,617,930 A | 10/1986 | Saunders |
| 4,759,350 A | 7/1988 | Dunn et al. |
| 4,768,504 A | 9/1988 | Ender |
| 4,872,095 A | 10/1989 | Dubak et al. |
| 4,952,213 A | 8/1990 | Bowman et al. |
| 5,086,401 A | 2/1992 | Glassman et al. |
| 5,087,261 A | 2/1992 | Ryd et al. |
| 5,092,869 A | 3/1992 | Waldron |
| 5,116,338 A | 5/1992 | Poggie et al. |
| 5,116,344 A | 5/1992 | Sundqvist |
| 5,122,142 A | 6/1992 | Pascaloff et al. |
| 5,147,365 A | 9/1992 | Whitlock et al. |
| 5,163,949 A | 11/1992 | Bonutti |
| 5,178,626 A | 1/1993 | Pappas et al. |
| 5,197,488 A | 3/1993 | Kovacevic |
| 5,201,749 A | 4/1993 | Sachse et al. |
| 5,207,711 A | 5/1993 | Caspari et al. |
| 5,213,112 A | 5/1993 | Niwa et al. |
| 5,263,972 A | 11/1993 | Evans et al. |
| 5,306,285 A | 4/1994 | Miller et al. |
| 5,344,461 A | 9/1994 | Phlipot |
| 5,360,016 A | 11/1994 | Kovacevic |
| 5,382,249 A | 1/1995 | Fletcher et al. |
| 5,403,318 A | 4/1995 | Boehringer et al. |
| 5,409,491 A | 4/1995 | Boehringer et al. |
| 5,437,676 A | 8/1995 | Bouraly et al. |
| 5,439,472 A | 8/1995 | Evans et al. |
| 5,454,406 A | 10/1995 | Reret et al. |
| 5,464,406 A | 11/1995 | Ritter et al. |
| 5,470,354 A | 11/1995 | Hershberger et al. |
| 5,486,178 A | 1/1996 | Hodge |
| 5,489,311 A | 2/1996 | Cipolletti |
| 5,496,325 A | 3/1996 | Mclees |
| 5,507,763 A | 4/1996 | Petersen et al. |
| 5,514,183 A | 5/1996 | Epstein |
| 5,520,695 A | 5/1996 | Luckman |
| 5,540,696 A | 7/1996 | Booth, Jr. et al. |
| 5,554,165 A | 9/1996 | Raitt et al. |
| 5,562,675 A | 10/1996 | Mcnulty et al. |
| 5,569,257 A | 10/1996 | Arnegger et al. |
| 5,597,379 A | 1/1997 | Haines et al. |
| 5,624,444 A | 4/1997 | Wixon et al. |
| 5,630,820 A | 5/1997 | Todd |
| 5,649,929 A | 7/1997 | Callaway |
| 5,656,785 A | 8/1997 | Trainor et al. |
| 5,662,656 A | 9/1997 | White |
| 5,669,914 A | 9/1997 | Eckhoff |
| 5,681,316 A | 10/1997 | DeOrio et al. |
| 5,688,280 A | 11/1997 | Booth, Jr. et al. |
| 5,688,282 A | 11/1997 | Baron et al. |
| 5,702,464 A | 12/1997 | Lackey et al. |
| 5,720,752 A | 2/1998 | Elliot et al. |
| 5,733,292 A | 3/1998 | Gustilo et al. |
| 5,735,866 A | 4/1998 | Adams et al. |
| 5,735,904 A | 4/1998 | Pappas |
| 5,755,801 A | 5/1998 | Walker et al. |
| 5,776,137 A | 7/1998 | Katz |
| 5,782,925 A | 7/1998 | Collazo et al. |
| 5,800,438 A | 9/1998 | Tuke et al. |
| 5,839,196 A | 11/1998 | Trott |
| 5,846,244 A | 12/1998 | Cripe |
| 5,860,980 A | 1/1999 | Axelson, Jr. et al. |
| 5,879,394 A | 3/1999 | Ashby et al. |
| 5,880,976 A | 3/1999 | DiGioia, III et al. |
| 5,885,298 A | 3/1999 | Herrington et al. |
| 5,911,723 A | 6/1999 | Ashby et al. |
| 5,916,220 A | 6/1999 | Masini |
| 6,022,353 A | 2/2000 | Fletcher et al. |
| 6,022,377 A | 2/2000 | Nuelle et al. |
| 6,033,415 A | 3/2000 | Mittelstadt et al. |
| 6,056,756 A | 5/2000 | Eng et al. |
| 6,063,091 A | 5/2000 | Lombardo et al. |
| 6,068,658 A | 5/2000 | Insall et al. |
| 6,077,270 A | 6/2000 | Katz |
| 6,090,114 A | 7/2000 | Matsuno et al. |
| 6,096,043 A | 8/2000 | Techiera et al. |
| 6,096,082 A | 8/2000 | Stegmuller et al. |
| 6,296,666 B1 | 10/2001 | Gardner |
| 6,361,564 B1 | 3/2002 | Marceaux et al. |
| 6,478,753 B2 | 11/2002 | Reay-young |
| 6,488,711 B1 | 12/2002 | Grafinger |
| 6,503,253 B1 | 1/2003 | Fletcher et al. |
| 6,506,215 B1 | 1/2003 | Letot et al. |
| 6,514,259 B2 | 2/2003 | Picard et al. |
| 6,558,427 B2 | 5/2003 | Leclercq et al. |
| 6,575,980 B1 | 6/2003 | Robie et al. |
| 6,595,997 B2 | 7/2003 | Axelson, Jr. et al. |
| 6,632,225 B2 | 10/2003 | Sanford et al. |
| 6,648,896 B2 | 11/2003 | Overes et al. |
| 6,656,186 B2 | 12/2003 | Meckel |
| 6,723,101 B2 | 4/2004 | Fletcher et al. |
| 6,758,850 B2 | 7/2004 | Smith et al. |
| 6,846,230 B2 | 1/2005 | Jonas |
| 6,875,222 B2 | 4/2005 | Long et al. |
| 6,896,679 B2 | 5/2005 | Danger et al. |
| 6,916,325 B2 | 7/2005 | Kana et al. |
| 6,972,039 B2 | 12/2005 | Metzger et al. |
| 6,984,249 B2 | 1/2006 | Keller |
| 7,097,662 B2 | 8/2006 | Evans, III et al. |
| 7,101,377 B2 | 9/2006 | Cortellessa et al. |
| 7,101,401 B2 | 9/2006 | Brack |
| 7,104,996 B2 | 9/2006 | Bonutti |
| 7,261,719 B1 | 8/2007 | Twomey et al. |
| 7,374,563 B2 | 5/2008 | Roger et al. |
| 7,412,897 B2 | 8/2008 | Crottet et al. |
| 7,442,196 B2 | 10/2008 | Fisher et al. |
| 7,488,324 B1 | 2/2009 | Metzger et al. |
| 7,497,860 B2 | 3/2009 | Carusillo et al. |
| 7,527,628 B2 | 5/2009 | Fletcher et al. |
| 7,575,602 B2 | 8/2009 | Amirouche et al. |
| 7,578,821 B2 | 8/2009 | Fisher et al. |
| 7,615,055 B2 | 11/2009 | DiSilvestro |
| 7,704,254 B2 | 4/2010 | Walen et al. |
| 7,837,691 B2 | 11/2010 | Cordes et al. |
| 7,857,821 B2 | 12/2010 | Couture et al. |
| 7,949,386 B2 | 5/2011 | Buly et al. |
| 8,007,448 B2 | 8/2011 | Moctesuma de La Barrera |
| 8,065,927 B2 | 11/2011 | Crottet et al. |
| 8,118,815 B2 | 2/2012 | Van Der Walt |
| 8,211,041 B2 | 7/2012 | Fisher et al. |
| 8,265,790 B2 | 9/2012 | Amiot et al. |
| 8,265,949 B2 | 9/2012 | Haddad |
| 8,323,290 B2 | 12/2012 | Metzger et al. |
| 8,337,508 B2 | 12/2012 | Lavallee et al. |
| 8,394,104 B2 | 3/2013 | DiSilvestro |
| 8,407,067 B2 | 3/2013 | Uthgenannt et al. |
| 8,435,246 B2 | 5/2013 | Fisher et al. |
| 8,491,589 B2 | 7/2013 | Fisher et al. |

(56) References Cited

U.S. PATENT DOCUMENTS

| | | |
|---|---|---|
| 8,506,571 B2 | 8/2013 | Chana et al. |
| 8,532,807 B2 | 9/2013 | Metzger |
| 8,556,830 B2 | 10/2013 | Sherman et al. |
| 8,591,516 B2 | 11/2013 | Metzger et al. |
| 8,715,290 B2 | 5/2014 | Fisher et al. |
| 8,734,454 B2 | 5/2014 | DiSilvestro |
| 8,758,355 B2 | 6/2014 | Fisher et al. |
| 8,828,013 B2 | 9/2014 | Fisher et al. |
| 8,884,618 B2 | 11/2014 | Mahfouz |
| 8,888,718 B2 | 11/2014 | Siston et al. |
| 9,050,197 B2 | 6/2015 | Lorio et al. |
| 9,095,352 B2 | 8/2015 | Fisher et al. |
| 9,232,951 B2 | 1/2016 | Johannaber |
| 9,259,172 B2 | 2/2016 | Stein et al. |
| 9,265,447 B2 | 2/2016 | Stein et al. |
| 9,320,642 B1 | 4/2016 | Van Oudenallen et al. |
| 9,351,850 B2 | 5/2016 | Fisher et al. |
| 9,439,656 B2 | 9/2016 | Chana et al. |
| 9,572,588 B2 | 2/2017 | Fisher et al. |
| 9,585,615 B2 | 3/2017 | Singh et al. |
| 9,622,761 B2 | 4/2017 | Chana et al. |
| 9,693,783 B2 | 7/2017 | Fisher et al. |
| 9,730,810 B2 | 8/2017 | Fisher |
| 9,808,356 B2 | 11/2017 | Haight et al. |
| 9,980,735 B2 | 5/2018 | Chana et al. |
| 9,993,354 B2 | 6/2018 | Fisher et al. |
| 10,172,723 B2 | 1/2019 | Fisher et al. |
| 10,485,554 B2 | 11/2019 | Chana et al. |
| 10,555,822 B2 | 2/2020 | Fisher et al. |
| 2002/0029045 A1 | 3/2002 | Bonutti |
| 2002/0052606 A1 | 5/2002 | Bonutti |
| 2002/0116022 A1 | 8/2002 | Lebouitz et al. |
| 2002/0133161 A1 | 9/2002 | Axelson, Jr. et al. |
| 2002/0133175 A1 | 9/2002 | Carson |
| 2002/0198530 A1 | 12/2002 | Sanford et al. |
| 2002/0198556 A1 | 12/2002 | Ark et al. |
| 2003/0014067 A1 | 1/2003 | Kullmer et al. |
| 2003/0028196 A1 | 2/2003 | Bonutti |
| 2003/0045883 A1 | 3/2003 | Chow et al. |
| 2003/0069644 A1 | 4/2003 | Kovacevic et al. |
| 2003/0075162 A1 | 4/2003 | Hamilton |
| 2003/0130665 A1 | 7/2003 | Pinczewski et al. |
| 2003/0153978 A1 | 8/2003 | Whiteside |
| 2003/0157083 A1 | 8/2003 | Udell et al. |
| 2003/0187452 A1 | 10/2003 | Smith et al. |
| 2004/0019382 A1 | 1/2004 | Amirouche et al. |
| 2004/0024311 A1 | 2/2004 | Arthur, III |
| 2004/0039396 A1 | 2/2004 | Couture et al. |
| 2004/0039398 A1 | 2/2004 | Cortellessa et al. |
| 2004/0064073 A1 | 4/2004 | Heldreth |
| 2004/0064191 A1 | 4/2004 | Wasielewski |
| 2004/0097951 A1 | 5/2004 | Steffensmeier |
| 2004/0149282 A1 | 8/2004 | Hickle |
| 2004/0167450 A1 | 8/2004 | Buckman et al. |
| 2004/0172044 A1 | 9/2004 | Grimm et al. |
| 2004/0199167 A1 | 10/2004 | Fletcher et al. |
| 2004/0236424 A1 | 11/2004 | Berez et al. |
| 2004/0243136 A1 | 12/2004 | Gupta et al. |
| 2005/0010300 A1 | 1/2005 | Disilvestro et al. |
| 2005/0010302 A1 | 1/2005 | Dietz et al. |
| 2005/0021039 A1 | 1/2005 | Cusick et al. |
| 2005/0065530 A1 | 3/2005 | Stauch et al. |
| 2005/0070897 A1 | 3/2005 | Petersen |
| 2005/0113840 A1 | 5/2005 | Metzger et al. |
| 2005/0113846 A1 | 5/2005 | Carson |
| 2005/0113932 A1 | 5/2005 | Kovacevic |
| 2005/0119661 A1 | 6/2005 | Hodgson et al. |
| 2005/0143746 A1 | 6/2005 | Steffensmeier et al. |
| 2005/0149042 A1 | 7/2005 | Metzger |
| 2005/0177170 A1 | 8/2005 | Fisher et al. |
| 2005/0209605 A1 | 9/2005 | Grimm et al. |
| 2005/0222573 A1 | 10/2005 | Branch et al. |
| 2005/0240196 A1 | 10/2005 | Davis et al. |
| 2005/0267485 A1 | 12/2005 | Cordes et al. |
| 2006/0081063 A1 | 4/2006 | Neubauer et al. |
| 2006/0241569 A1 | 10/2006 | Disilvestro |
| 2006/0241639 A1 | 10/2006 | Kuczynski et al. |
| 2006/0241640 A1 | 10/2006 | Briard et al. |
| 2007/0043375 A1 | 2/2007 | Anissian |
| 2007/0073305 A1 | 3/2007 | Lionberger et al. |
| 2007/0083209 A1 | 4/2007 | Schenberger et al. |
| 2007/0119055 A1 | 5/2007 | Walen et al. |
| 2007/0123893 A1 | 5/2007 | O' Donoghue |
| 2007/0198022 A1 | 8/2007 | Lang et al. |
| 2007/0219559 A1 | 9/2007 | Heavener et al. |
| 2007/0232959 A1 | 10/2007 | Couture et al. |
| 2007/0234819 A1 | 10/2007 | Amirouche et al. |
| 2007/0239165 A1 | 10/2007 | Amirouche |
| 2007/0244488 A1 | 10/2007 | Metzger et al. |
| 2007/0282451 A1 | 12/2007 | Metzger et al. |
| 2007/0293868 A1 | 12/2007 | Delfosse et al. |
| 2008/0009697 A1 | 1/2008 | Haider et al. |
| 2008/0027449 A1 | 1/2008 | Gundlapalli et al. |
| 2008/0065085 A1 | 3/2008 | Couture et al. |
| 2008/0065225 A1 | 3/2008 | Wasielewski et al. |
| 2008/0119891 A1 | 5/2008 | Miles et al. |
| 2008/0177261 A1 | 7/2008 | Mcminn |
| 2008/0195109 A1 | 8/2008 | Hunter et al. |
| 2008/0243125 A1 | 10/2008 | Guzman et al. |
| 2008/0306413 A1 | 12/2008 | Crottet et al. |
| 2009/0004331 A1 | 2/2009 | Rasmussen |
| 2009/0093814 A1 | 4/2009 | Fletcher et al. |
| 2009/0093815 A1 | 4/2009 | Fletcher et al. |
| 2009/0157083 A1 | 6/2009 | Park et al. |
| 2009/0234360 A1 | 9/2009 | Alexander |
| 2010/0023067 A1 | 1/2010 | DiSilvestro et al. |
| 2010/0063508 A1 | 3/2010 | Borja et al. |
| 2010/0063509 A1 | 3/2010 | Borja et al. |
| 2010/0069911 A1 | 3/2010 | Borja et al. |
| 2010/0198275 A1 | 8/2010 | Chana et al. |
| 2010/0249658 A1 | 9/2010 | Sherman |
| 2010/0249787 A1 | 9/2010 | Roche |
| 2010/0249791 A1 | 9/2010 | Roche |
| 2010/0256479 A1 | 10/2010 | Park et al. |
| 2010/0332152 A1 | 12/2010 | Stein |
| 2011/0092804 A1 | 4/2011 | Schoenefeld et al. |
| 2011/0106091 A1 | 5/2011 | Fisher et al. |
| 2011/0106092 A1 | 5/2011 | Fisher et al. |
| 2011/0295378 A1 | 12/2011 | Bojarski et al. |
| 2012/0184961 A1 | 7/2012 | Johannaber |
| 2012/0232429 A1 | 9/2012 | Fischer et al. |
| 2012/0245589 A1 | 9/2012 | Fisher et al. |
| 2012/0259342 A1 | 10/2012 | Chana et al. |
| 2013/0013075 A1 | 1/2013 | Fisher et al. |
| 2013/0013076 A1 | 1/2013 | Fisher et al. |
| 2013/0023794 A1 | 1/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0289570 A1 | 10/2013 | Chao |
| 2013/0296860 A1 | 11/2013 | Chana et al. |
| 2014/0276240 A1 | 9/2014 | Stein et al. |
| 2015/0100059 A1 | 4/2015 | Chana et al. |
| 2015/0106024 A1 | 4/2015 | Lightcap et al. |
| 2015/0230804 A1 | 8/2015 | Chana et al. |
| 2015/0289884 A1 | 10/2015 | Fisher et al. |
| 2015/0313725 A1 | 11/2015 | Fisher et al. |
| 2016/0045317 A1 | 2/2016 | Lang et al. |
| 2016/0346044 A1 | 12/2016 | Brown et al. |
| 2017/0042554 A1 | 2/2017 | Chana et al. |
| 2017/0119549 A1 | 5/2017 | Fisher et al. |
| 2017/0367848 A1 | 12/2017 | Fisher et al. |
| 2020/0390501 A1 | 12/2020 | Brown et al. |

FOREIGN PATENT DOCUMENTS

| | | |
|---|---|---|
| CA | 2555283 C | 7/2014 |
| CN | 1913844 A | 2/2007 |
| CN | 101415371 A | 4/2009 |
| CN | 101815477 A | 8/2010 |
| CN | 102365061 A | 2/2012 |
| CN | 104302234 A | 1/2015 |
| CN | 104302234 B | 12/2016 |
| CN | 108040464 A | 5/2018 |

(56) References Cited

FOREIGN PATENT DOCUMENTS

| | | |
|---|---|---|
| EP | 979636 A2 | 2/2000 |
| EP | 1304093 A1 | 4/2003 |
| EP | 1402857 A2 | 3/2004 |
| EP | 1444957 A1 | 8/2004 |
| EP | 2138107 A1 | 12/2009 |
| EP | 1718232 B1 | 10/2012 |
| EP | 2567664 A2 | 3/2013 |
| EP | 2567665 A2 | 3/2013 |
| EP | 2822481 A1 | 1/2015 |
| EP | 2665428 B1 | 8/2016 |
| EP | 2822481 B1 | 12/2016 |
| FR | 2917284 A1 | 12/2008 |
| JP | H11513274 A | 11/1999 |
| JP | 2008517708 A | 5/2008 |
| JP | 2010502389 A | 1/2010 |
| JP | 2010526605 A | 8/2010 |
| JP | 2011506040 A | 3/2011 |
| JP | 2007520317 A | 5/2012 |
| JP | 2018525045 A | 9/2018 |
| KR | 1158952 | 6/2012 |
| WO | WO-9104715 A1 | 4/1991 |
| WO | WO-9709939 A1 | 3/1997 |
| WO | WO-9832384 A1 | 7/1998 |
| WO | WO-03079940 A2 | 10/2003 |
| WO | WO-2005037121 A1 | 4/2005 |
| WO | WO-2005089681 A2 | 9/2005 |
| WO | WO-2005122899 A1 | 12/2005 |
| WO | WO-2006047005 A2 | 5/2006 |
| WO | WO-2007030793 A2 | 3/2007 |
| WO | WO-2008030842 A2 | 3/2008 |
| WO | WO-2008073999 A2 | 6/2008 |
| WO | WO-2013013170 A1 | 1/2013 |
| WO | WO-2013063043 A1 | 5/2013 |
| WO | WO-2013134595 A1 | 9/2013 |
| WO | WO-2013188960 A1 | 12/2013 |
| WO | WO-2016191713 A1 | 12/2016 |

OTHER PUBLICATIONS

"U.S. Appl. No. 13,659,280, Response filed Nov. 23, 2016 to Non Final Office Action dated Aug. 25, 2016", 10 pgs.
"U.S. Appl. No. 13/659,280, Advisory Action dated May 25, 2017", 3 pgs.
"U.S. Appl. No. 13/659,280, Decision on Pre-Appeal Brief Request May 18, 2016", 2 pgs.
"U.S. Appl. No. 13/659,280, Examiner Interview Summary dated Nov. 1, 2016", 3 pgs.
"U.S. Appl. No. 13/659,280, Final Office Action dated Feb. 3, 2016", 12 pgs.
"U.S. Appl. No. 13/659,280, Final Office Action dated Mar. 4, 2015", 13 pgs.
"U.S. Appl. No. 13/659,280, Final Office Action dated Mar. 7, 2017", 13 pgs.
"U.S. Appl. No. 13/659,280, Non Final Office Action dated Aug. 25, 2016", 11 pgs.
"U.S. Appl. No. 13/659,280, Non Final Office Action dated Oct. 10, 2014", 16 pgs.
"U.S. Appl. No. 13/659,280, Notice of Allowance dated Jul. 7, 2017", 9 pgs.
"U.S. Appl. No. 13/659,280, Pre-Appeal Brief Request filed May 2, 2016", 5 pgs.
"U.S. Appl. No. 13/659,280, Pre-Appeal Brief Request filed Jun. 7, 2017", 5 pgs.
"U.S. Appl. No. 13/659,280, Response filed Jan. 12, 2015 to Non Final Office Action dated Oct. 10, 2014", 13 pgs.
"U.S. Appl. No. 13/659,280, Response filed May 8, 2017 to Final Office Action dated Mar. 7, 2017", 11 pgs.
"U.S. Appl. No. 13/659,280, Response filed May 20, 2015 to Final Office Action dated Mar. 4, 2015", 10 pgs.
"International Application Serial No. PCT/US2012/061588, International Preliminary Report on Patentability dated Oct. 21, 2013", 6 pgs.
"International Application Serial No. PCT/US2012/061588, International Search Report dated Jan. 3, 2013", 10 pgs.
"International Application Serial No. PCT/US2012/061588, Written Opinion dated Jan. 3, 2013", 8 pgs.
"U.S. Appl. No. 10/773,608, Advisory Action dated Mar. 7, 2007", 3 pgs.
"U.S. Appl. No. 10/773,608, Examiner Interview Summary dated Jul. 13, 2007", 4 pgs.
"U.S. Appl. No. 10/773,608, Examiner Interview Summary dated Jul. 19, 2006", 3 pgs.
"U.S. Appl. No. 10/773,608, Examiner Interview Summary dated Aug. 1, 2006", 4 pgs.
"U.S. Appl. No. 10/773,608, Final Office Action dated Jun. 12, 2008", 5 pgs.
"U.S. Appl. No. 10/773,608, Final Office Action dated Oct. 16, 2007", 10 pgs.
"U.S. Appl. No. 10/773,608, Final Office Action dated Dec. 1, 2006", 8 pgs.
"U.S. Appl. No. 10/773,608, Non Final Office Action dated Jan. 24, 2008", 6 pgs.
"U.S. Appl. No. 10/773,608, Non Final Office Action dated Jun. 4, 2007", 9 pgs.
"U.S. Appl. No. 10/773,608, Non Final Office Action dated Jun. 27, 2006", 10 pgs.
"U.S. Appl. No. 10/773,608, Notice of Allowance dated Sep. 5, 2008", 9 pgs.
"U.S. Appl. No. 10/773,608, Response filed Feb. 12, 2008 to Non Final Office Action dated Jan. 24, 2008", 11 pgs.
"U.S. Appl. No. 10/773,608, Response filed Feb. 13, 2007 to Final Office Action dated Dec. 1, 2006", 17 pgs.
"U.S. Appl. No. 10/773,608, Response filed Apr. 12, 2006 to Restriction Requirement dated Mar. 20, 2006", 22 pgs.
"U.S. Appl. No. 10/773,608, Response filed Jun. 18, 2008 to Final Office Action dated Jun. 12, 2008", 10 pgs.
"U.S. Appl. No. 10/773,608, Response filed Jul. 19, 2007 to Non Final Office Action dated Jun. 4, 2007", 17 pgs.
"U.S. Appl. No. 10/773,608, Response filed Sep. 15, 2006 to Non Final Office Action dated Jun. 27, 2006", 24 pgs.
"U.S. Appl. No. 10/773,608, Response filed Oct. 29, 2007 to Final Office Action dated Oct. 16, 2007", 12 pgs.
"U.S. Appl. No. 10/773,608, Restriction Requirement dated Mar. 20, 2006", 6 pgs.
"U.S. Appl. No. 10/973,936, Final Office Action dated Aug. 7, 2008", 5 pgs.
"U.S. Appl. No. 10/973,936, Non Final Office Action dated Jan. 6, 2009", 6 pgs.
"U.S. Appl. No. 10/973,936, Non Final Office Action dated Nov. 27, 2007", 7 pgs.
"U.S. Appl. No. 10/973,936, Notice of Allowance dated Jul. 9, 2009", 4 pgs.
"U.S. Appl. No. 10/973,936, Response filed Mar. 18, 2009 to Non Final Office Action dated Jan. 6, 2009", 8 pgs.
"U.S. Appl. No. 10/973,936, Response filed Mar. 27, 2008 to Non Final Office Action dated Nov. 27, 2007", 10 pgs.
"U.S. Appl. No. 10/973,936, Response filed Aug. 31, 2007 to Restriction Requirement dated Jul. 30, 2007", 5 pgs.
"U.S. Appl. No. 10/973,936, Response filed Oct. 7, 2008 to Final Office Action dated Aug. 7, 2008", 8 pgs.
"U.S. Appl. No. 10/973,936, Restriction Requirement dated Jul. 30, 2007", 5 pgs.
"U.S. Appl. No. 11/149,944, Non Final Office Action dated Dec. 29, 2009", 7 pgs.
"U.S. Appl. No. 11/149,944, Notice of Allowance dated Jul. 12, 2010", 5 pgs.
"U.S. Appl. No. 11/149,944, Response filed Feb. 19, 2010 to Non Final Office Action dated Dec. 29, 2009", 13 pgs.
"U.S. Appl. No. 12/511,527, Advisory Action dated Jun. 7, 2013", 3 pgs.
"U.S. Appl. No. 12/511,527, Appeal Brief filed Aug. 20, 2013", 16 pgs.
"U.S. Appl. No. 12/511,527, Examiner Interview Summary dated May 16, 2013", 3 pgs.

(56) References Cited

OTHER PUBLICATIONS

"U.S. Appl. No. 12/511,527, Final Office Action dated Mar. 21, 2013", 10 pgs.
"U.S. Appl. No. 12/511,527, Non Final Office Action dated Sep. 4, 2012", 16 pgs.
"U.S. Appl. No. 12/511,527, Notice of Allowance dated Dec. 18, 2013", 18 pgs.
"U.S. Appl. No. 12/511,527, Response filed May 15, 2013 to Final Office Action dated Mar. 21, 2013", 14 pgs.
"U.S. Appl. No. 12/511,527, Response filed Nov. 30, 2012 to Non Final Office Action dated Sep. 14, 2012", 16 pgs.
"U.S. Appl. No. 12/544,897, Final Office Action dated Apr. 17, 2012", 14 pgs.
"U.S. Appl. No. 12/544,897, Non Final Office Action dated Mar. 6, 2012", 10 pgs.
"U.S. Appl. No. 12/544,897, Notice of Allowance dated May 2, 2012", 5 pgs.
"U.S. Appl. No. 12/544,897, Response filed Feb. 17, 2012 to Restriction Requirement dated Jan. 17, 2012", 2 pgs.
"U.S. Appl. No. 12/544,897, Response filed Mar. 26, 2012 to Non Final Office Action dated Mar. 6, 2012", 12 pgs.
"U.S. Appl. No. 12/544,897, Response filed Apr. 19, 2012 to Final Office Action dated Apr. 17, 2012", 10 pgs.
"U.S. Appl. No. 12/544,897, Restriction Requirement dated Jan. 17, 2012", 8 pgs.
"U.S. Appl. No. 12/609,666, Advisory Action dated Dec. 19, 2013", 3 pgs.
"U.S. Appl. No. 12/609,666, Examiner Interview Summary dated May 23, 2013", 3 pgs.
"U.S. Appl. No. 12/609,666, Final Office Action dated Feb. 26, 2015", 10 pgs.
"U.S. Appl. No. 12/609,666, Final Office Action dated Oct. 4, 2013", 10 pgs.
"U.S. Appl. No. 12/609,666, Non Final Office Action dated Feb. 14, 2013", 12 pgs.
"U.S. Appl. No. 12/609,666, Non Final Office Action dated Jun. 26, 2014", 9 pgs.
"U.S. Appl. No. 12/609,666, Non Final Office Action dated Oct. 11, 2012", 10 pgs.
"U.S. Appl. No. 12/609,666, Response filed Jan. 6, 2014 to Advisory Action dated Dec. 19, 2013", 10 pgs.
"U.S. Appl. No. 12/609,666, Response filed Jan. 11, 2013 to Non Final Office Action dated Oct. 11, 2012", 14 pgs.
"U.S. Appl. No. 12/609,666, Response filed May 14, 2013 to Non Final Office Action dated Feb. 14, 2013", 12 pgs.
"U.S. Appl. No. 12/609,666, Response filed May 22, 2012 to Restriction Requirement dated May 11, 2012", 2 pgs.
"U.S. Appl. No. 12/609,666, Response filed Oct. 27, 2014 to Non-Final Office Action dated Jun. 26, 2014", 11 pgs.
"U.S. Appl. No. 12/609,666, Response filed Dec. 4, 2013 to Final Office Action dated Oct. 4, 2013", 10 pgs.
"U.S. Appl. No. 12/609,666, Restriction Requirement dated May 11, 2012", 8 pgs.
"U.S. Appl. No. 12/616,747, Examiner Interview Summary dated Jul. 31, 2012", 3 pgs.
"U.S. Appl. No. 12/616,747, Final Office Action dated Apr. 20, 2012", 11 pgs.
"U.S. Appl. No. 12/616,747, Non Final Office Action dated Mar. 15, 2012", 12 pgs.
"U.S. Appl. No. 12/616,747, Notice of Allowance dated Jan. 10, 2013", 7 pgs.
"U.S. Appl. No. 12/616,747, Notice of Allowance dated Sep. 28, 2012", 10 pgs.
"U.S. Appl. No. 12/616,747, Preliminary Amendment filed Nov. 11, 2009", 10 pgs.
"U.S. Appl. No. 12/616,747, Response filed Mar. 30, 2012 to Non Final Office Action dated Mar. 15, 2012", 12 pgs.
"U.S. Appl. No. 12/616,747, Response filed Aug. 15, 2012 to Final Office Action dated Apr. 20, 2012", 10 pgs.
"U.S. Appl. No. 12/729,222, Final Office Action dated Nov. 15, 2012", 12 pgs.
"U.S. Appl. No. 12/729,222, Non Final Office Action dated Jan. 9, 2014", 14 pgs.
"U.S. Appl. No. 12/729,222, Non Final Office Action dated Jul. 13, 2012", 10 pgs.
"U.S. Appl. No. 12/729,222, Notice of Allowance dated May 1, 2014", 5 pgs.
"U.S. Appl. No. 12/729,222, Response filed Feb. 14, 2013 to Final Office Action dated Nov. 15, 2012", 10 pgs.
"U.S. Appl. No. 12/729,222, Response filed Apr. 8, 2014 to Non-Final Office Action dated Jan. 9, 2014", 8 pgs.
"U.S. Appl. No. 12/729,222, Response filed Jun. 4, 2012 to Restriction Requirement dated May 3, 2012", 2 pgs.
"U.S. Appl. No. 12/729,222, Response filed Oct. 12, 2012 to Non Final Office Action dated Jul. 13, 2012", 8 pgs.
"U.S. Appl. No. 12/729,222, Restriction Requirement dated May 3, 2012", 6 pgs.
"U.S. Appl. No. 12/757,486, Final Office Action dated May 17, 2012", 10 pgs.
"U.S. Appl. No. 12/757,486, Non Final Office Action dated Apr. 10, 2012", 10 pgs.
"U.S. Appl. No. 12/757,486, Notice of Allowance dated Apr. 10, 2013", 11 pgs.
"U.S. Appl. No. 12/757,486, Response filed Mar. 23, 2012 to Restriction Requirement dated Mar. 14, 2012", 2 pgs.
"U.S. Appl. No. 12/757,486, Response filed Apr. 25, 2012 to Non Final Office Action dated Apr. 10, 2012", 25 pgs.
"U.S. Appl. No. 12/757,486, Response filed May 21, 2012 to Final Office Action dated May 17, 2012", 9 pgs.
"U.S. Appl. No. 12/757,486, Restriction Requirement dated Mar. 14, 2012", 9 pgs.
"U.S. Appl. No. 13/009,148, Examiner Interview Summary dated Feb. 26, 2015", 3 pgs.
"U.S. Appl. No. 13/009,148, Final Office Action dated Jun. 26, 2015", 6 pgs.
"U.S. Appl. No. 13/009,148, Non Final Office Action dated Mar. 26, 2014", 7 pgs.
"U.S. Appl. No. 13/009,148, Non Final Office Action dated Dec. 4, 2014", 10 pgs.
"U.S. Appl. No. 13/009,148, Notice of Allowance dated Sep. 25, 2015", 5 pgs.
"U.S. Appl. No. 13/009,148, Response filed Mar. 3, 2015 to Non-Final Office Action dated Dec. 4, 2014", 13 pgs.
"U.S. Appl. No. 13/009,148, Response filed Jun. 20, 2014 to Non-Final Office Action dated Mar. 26, 2014", 11 pgs.
"U.S. Appl. No. 13/009,148, Response filed Aug. 26, 2015 to Final Office Action dated Jun. 26, 2015", 10 pgs.
"U.S. Appl. No. 13/009,148, Response filed Nov. 7, 2013 to Restriction Requirement dated Oct. 11, 2013", 8 pgs.
"U.S. Appl. No. 13/009,148, Restriction Requirement dated Oct. 11, 2013", 6 pgs.
"U.S. Appl. No. 13/417,079, Advisory Action dated Jun. 13, 2014", 3 pgs.
"U.S. Appl. No. 13/417,079, Examiner Interview Summary dated Mar. 4, 2015", 3 pgs.
"U.S. Appl. No. 13/417,079, Final Office Action dated Apr. 10, 2014", 20 pgs.
"U.S. Appl. No. 13/417,079, Non Final Office Action dated Nov. 15, 2013", 12 pgs.
"U.S. Appl. No. 13/417,079, Non Final Office Action dated Nov. 26, 2014", 20 pgs.
"U.S. Appl. No. 13/417,079, Notice of Allowance dated Mar. 30, 2015", 8 pgs.
"U.S. Appl. No. 13/417,079, Response filed Feb. 26, 2015 to Non-Final Office Action dated Nov. 26, 2014", 16 pgs.
"U.S. Appl. No. 13/417,079, Response filed Mar. 14, 2014 to Non-Final Office action dated Nov. 15, 2013", 13 pgs.
"U.S. Appl. No. 13/417,079, Response filed Jun. 3, 2014 to Final Office Action dated Apr. 10, 2014", 13 pgs.
"U.S. Appl. No. 13/417,079, Response filed Oct. 25, 2013 to Restriction Requirement dated Sep. 25, 2013", 9 pgs.

(56) References Cited

OTHER PUBLICATIONS

"U.S. Appl. No. 13/417,079, Restriction Requirement dated Sep. 25, 2013", 6 pgs.
"U.S. Appl. No. 13/472,785, Appeal Brief filed Jun. 4, 2014", 17 pgs.
"U.S. Appl. No. 13/472,785, Appeal Decision dated Nov. 3, 2017", 6 pgs.
"U.S. Appl. No. 13/472,785, Examiner's Answer dated Jul. 31, 2014", 5 pgs.
"U.S. Appl. No. 13/472,785, Final Office Action dated Dec. 13, 2013", 10 pgs.
"U.S. Appl. No. 13/472,785, Non Final Office Action dated Jul. 16, 2013", 11 pgs.
"U.S. Appl. No. 13/472,785, Notice of Allowance dated Feb. 12, 2018", 7 pgs.
"U.S. Appl. No. 13/472,785, Preliminary Amendment dated Sep. 13, 2012", 9 pgs.
"U.S. Appl. No. 13/472,785, Response filed Sep. 30, 2014 to Examiner's Answer dated Jul. 31, 2014", 4 pgs.
"U.S. Appl. No. 13/472,785, Response filed Oct. 9, 2013 to Non Final Office Action dated Jul. 16, 2013", 15 pgs.
"U.S. Appl. No. 13/524,405, Advisory Action dated Oct. 7, 2015", 3 pgs.
"U.S. Appl. No. 13/524,405, Examiner Interview Summary dated Sep. 24, 2015", 3 pgs.
"U.S. Appl. No. 13/524,405, Final Office Action dated Jul. 30, 2015", 8 pgs.
"U.S. Appl. No. 13/524,405, Non Final Office Action dated Dec. 31, 2014", 8 pgs.
"U.S. Appl. No. 13/524,405, Notice of Allowance dated May 17, 2016", 7 pgs.
"U.S. Appl. No. 13/524,405, Response filed Mar. 31, 2015 to Non-Final Office Action dated Dec. 31, 2014", 14 pgs.
"U.S. Appl. No. 13/524,405, Response filed Aug. 4, 2014 to Restriction Requirement dated Jun. 4, 2014", 12 pgs.
"U.S. Appl. No. 13/524,405, Response filed Sep. 24, 2015 to Final Office Action dated Jul. 30, 2015", 9 pgs.
"U.S. Appl. No. 13/524,405, Restriction Requirement dated Jun. 4, 2014", 9 pgs.
"U.S. Appl. No. 13/619,227, Notice of Allowance dated Feb. 20, 2014", 5 pgs.
"U.S. Appl. No. 13/619,227, Notice of Allowance dated Jul. 19, 2013", 11 pgs.
"U.S. Appl. No. 13/619,227, Preliminary Amendment filed Sep. 14, 2012", 3 pgs.
"U.S. Appl. No. 13/619,227, Response filed Apr. 1, 2013 to Restriction Requirement dated Feb. 27, 2013", 6 pgs.
"U.S. Appl. No. 13/619,227, Restriction Requirement dated Feb. 27, 2013", 6 pgs.
"U.S. Appl. No. 13/619,227, Supplementary Preliminary Amendment filed Sep. 24, 2012", 6 pgs.
"U.S. Appl. No. 13/619,269, Non Final Office Action dated Dec. 13, 2012", 13 pgs.
"U.S. Appl. No. 13/619,269, Notice of Allowance dated Mar. 22, 2013", 8 pgs.
"U.S. Appl. No. 13/619,269, Preliminary Amendment filed Sep. 14, 2012", 3 pgs.
"U.S. Appl. No. 13/619,269, Response filed Mar. 11, 2013 to Non Final Office Action dated Dec. 12, 2012", 12 pgs.
"U.S. Appl. No. 13/709,491, Ex Parte Quayle Action mailed Mar. 27, 2015", 4 pgs.
"U.S. Appl. No. 13/709,491, Notice of Allowance dated May 5, 2015", 8 pgs.
"U.S. Appl. No. 13/709,491, Preliminary Amendment dated Dec. 10, 2012", 3 pgs.
"U.S. Appl. No. 13/709,491, Response filed Apr. 27, 2015 to Ex Parte Quayle mailed Mar. 27, 2015", 8 pgs.
"U.S. Appl. No. 13/709,506, Advisory Action dated Oct. 19, 2015", 3 pgs.
"U.S. Appl. No. 13/709,506, Final Office Action dated Aug. 13, 2015", 13 pgs.
"U.S. Appl. No. 13/709,506, Non Final Office Action dated Jan. 20, 2016", 12 pgs.
"U.S. Appl. No. 13/709,506, Non Final Office Action dated Mar. 13, 2015", 12 pgs.
"U.S. Appl. No. 13/709,506, Notice of Allowance dated Jun. 20, 2016", 10 pgs.
"U.S. Appl. No. 13/709,506, Notice of Allowance dated Oct. 11, 2016", 5 pgs.
"U.S. Appl. No. 13/709,506, Preliminary Amendment filed Dec. 10, 2012", 3 pgs.
"U.S. Appl. No. 13/709,506, Response filed Mar. 10, 2016 to Non Final Office Action dated Jan. 20, 2016", 18 pgs.
"U.S. Appl. No. 13/709,506, Response filed May 12, 2015 to Non-Final Office Action dated Mar. 13, 2015", 14 pgs.
"U.S. Appl. No. 13/709,506, Response filed Oct. 13, 2015 to Final Office Action dated Aug. 13, 2015", 16 pgs.
"U.S. Appl. No. 13/709,506, Response filed Nov. 3, 2015 to Advisory Action dated Oct. 19, 2015", 16 pgs.
"U.S. Appl. No. 13/709,506, Response filed Nov. 14, 2014 to Restriction Requirement dated Oct. 8, 2014", 7 pgs.
"U.S. Appl. No. 13/709,506, Restriction Requirement dated Oct. 8, 2014", 6 pgs.
"U.S. Appl. No. 13/937,749, Non Final Office Action dated Sep. 17, 2014", 10 pgs.
"U.S. Appl. No. 14/692,117, Preliminary Amendment filed Apr. 22, 2015", 8 pgs.
"U.S. Appl. No. 14/564,451, Advisory Action dated Nov. 2, 2016", 3 pgs.
"U.S. Appl. No. 14/564,451, Final Office Action dated Aug. 22, 2016", 9 pgs.
"U.S. Appl. No. 14/564,451, Non Final Office Action dated Apr. 12, 2016", 12 pgs.
"U.S. Appl. No. 14/564,451, Notice of Allowance dated Dec. 9, 2016", 5 pgs.
"U.S. Appl. No. 14/564,451, Preliminary Amendment filed Dec. 10, 2014", 8 pgs.
"U.S. Appl. No. 14/564,451, Response filed Oct. 24, 2016 to Final Office Action dated Aug. 22, 2016", 10 pgs.
"U.S. Appl. No. 14/564,451, Response filed Nov. 22, 2016 to Advisory Action dated Nov. 2, 2016", 10 pgs.
"U.S. Appl. No. 14/692,117, Final Office Action dated Oct. 31, 2017", 6 pgs.
"U.S. Appl. No. 14/692,117, Non Final Office Action dated Jun. 9, 2017", 6 pgs.
"U.S. Appl. No. 14/692,117, Notice of Allowance dated Jan. 30, 2018", 6 pgs.
"U.S. Appl. No. 14/692,117, Response filed Feb. 1, 2017 to Restriction Requirement dated Dec. 1, 2016", 8 pgs.
"U.S. Appl. No. 14/692,117, Response filed Sep. 6, 2017 to Non Final Office Action dated Jun. 9, 2017", 10 pgs.
"U.S. Appl. No. 14/692,117, Response filed Dec. 28, 2017 to Final Office Action dated Oct. 31, 2017", 11 pgs.
"U.S. Appl. No. 14/692,117, Restriction Requirement dated Dec. 1, 2016", 6 pgs.
"U.S. Appl. No. 14/752,161, Non Final Office Action dated Nov. 14, 2016", 13 pgs.
"U.S. Appl. No. 14/752,161, Notice of Allowance dated Mar. 2, 2017", 6 pgs.
"U.S. Appl. No. 14/752,161, Preliminary Amendment filed Aug. 17, 2015", 7 pgs.
"U.S. Appl. No. 14/752,161, Response filed Feb. 13, 2017 to Non Final Office Action dated Nov. 14, 2016", 13 pgs.
"U.S. Appl. No. 14/796,168, Non Final Office Action dated Jan. 13, 2017", 5 pgs.
"U.S. Appl. No. 14/796,168, Notice of Allowance dated Apr. 14, 2017", 5 pgs.
"U.S. Appl. No. 14/796,168, Preliminary Amendment filed Jul. 13, 2015", 6 pgs.
"U.S. Appl. No. 14/796,168, Response filed Feb. 9, 2017 to Non Final Office Action dated Jan. 13, 2017", 6 pgs.

(56) References Cited

OTHER PUBLICATIONS

"U.S. Appl. No. 15/167,261, Advisory Action dated Jun. 27, 2019", 3 pgs.
"U.S. Appl. No. 15/167,261, Final Office Action dated Mar. 22, 2019", 19 pgs.
"U.S. Appl. No. 15/167,261, Final Office Action dated Apr. 30, 2020", 20 pgs.
"U.S. Appl. No. 15/167,261, Non Final Office Action dated Sep. 20, 2018", 16 pgs.
"U.S. Appl. No. 15/167,261, Non Final Office Action dated Oct. 31, 2019", 24 pgs.
"U.S. Appl. No. 15/167,261, Response filed Jan. 31, 2020 to Non Final Office Action dated Oct. 31, 2019", 15 pgs.
"U.S. Appl. No. 15/167,261, Response filed May 22, 2019 to Final Office Action dated Mar. 22, 2019", 14 pgs.
"U.S. Appl. No. 15/167,261, Response filed Dec. 20, 2018 to Non Final Office Action dated Sep. 20, 2018", 18 pgs.
"U.S. Appl. No. 15/239,029, Notice of Allowance dated Jul. 25, 2019", 9 pgs.
"U.S. Appl. No. 15/239,029, Preliminary Amendment filed Feb. 22, 2017", 7 pgs.
"U.S. Appl. No. 15/239,029, Response filed Dec. 17, 2018 to Restriction Requirement dated Oct. 18, 2018", 7 pgs.
"U.S. Appl. No. 15/239,029, Restriction Requirement dated Oct. 18, 2018", 6 pgs.
"U.S. Appl. No. 15/405,820, Appeal Brief filed Aug. 29, 2018", 28 pgs.
"U.S. Appl. No. 15/405,820, Appeal Decision dated Nov. 1, 2019", 10 pgs.
"U.S. Appl. No. 15/405,820, Appellant's Reply Brief filed Feb. 25, 2019", 6 pgs.
"U.S. Appl. No. 15/405,820, Examiner Interview Summary dated Mar. 15, 2018", 3 pgs.
"U.S. Appl. No. 15/405,820, Final Office Action dated May 16, 2018", 11 pgs.
"U.S. Appl. No. 15/405,820, Non Final Office Action dated Jun. 21, 2017", 11 pgs.
"U.S. Appl. No. 15/405,820, Non Final Office Action dated Dec. 14, 2017", 13 pgs.
"U.S. Appl. No. 15/405,820, Notice of Allowance dated Nov. 18, 2019", 5 pgs.
"U.S. Appl. No. 15/405,820, Pre-Appeal Brief Request filed Jul. 13, 2018", 5 pgs.
"U.S. Appl. No. 15/405,820, Preliminary Amendment filed Jan. 16, 2017", 8 pgs.
"U.S. Appl. No. 15/405,820, Response filed Mar. 9, 2018 to Non-Final Office Action dated Dec. 14, 2017", 10 pgs.
"U.S. Appl. No. 15/405,820, Response filed Apr. 24, 2017 to Restriction Requirement dated Mar. 8, 2017", 11 pgs.
"U.S. Appl. No. 15/405,820, Response filed Sep. 11, 2017 to Non-Final Office Action dated Jun. 21, 2017", 15 pgs.
"U.S. Appl. No. 15/405,820, Restriction Requirement dated Mar. 8, 2017", 6 pgs.
"U.S. Appl. No. 15/564,451, Response filed Jul. 11, 2016 to Non Final Office Action dated Apr. 12, 2016", 10 pgs.
"U.S. Appl. No. 15/647,937, Notice of Allowance dated Sep. 24, 2018", 8 pgs.
"U.S. Appl. No. 15/647,937, Preliminary Amendment filed Sep. 20, 2017", 7 pgs.
"Australian Application Serial No. 2005300099, Office Action dated Jan. 24, 2011", 2 pgs.
"Australian Application Serial No. 2005300099, Response filed Feb. 8, 2011 to Office Action dated Jan. 24, 2011", 19 pgs.
"Australian Application Serial No. 2009282789, Office Action dated Mar. 6, 2014", 5 pgs.
"Australian Application Serial No. 2009282789, Response filed Nov. 10, 2014 to Office Action dated Mar. 6, 2014", 26 pgs.
"Australian Application Serial No. 2009282789, Subsequent Examiners Report dated Jan. 2, 2015", 4 pgs.
"Australian Application Serial No. 2016267279, First Examination Report dated Jan. 10, 2020", 5 pgs.
"Canadian Application Serial No. 2,555,283, Office Action dated Dec. 4, 2012", 6 pgs.
"Canadian Application Serial No. 2,555,283, Response filed May 27, 2013 to Office Action dated Dec. 4, 2012", 23 pgs.
"Canadian Application Serial No. 2,555,283, Response filed Jun. 13, 2012 to Office Action dated Mar. 21, 2012", 15 pgs.
"Canadian Application Serial No. 2,585,862, Office Action dated Aug. 16, 2011", 3 pgs.
"Canadian Application Serial No. 2,585,862, Office Action dated Oct. 18, 2013", 4 pgs.
"Canadian Application Serial No. 2,585,862, Office Action dated Nov. 21, 2012", 5 pgs.
"Canadian Application Serial No. 2,585,862, Response filed Apr. 15, 2014 to Office Action dated Oct. 18, 2013", 9 pgs.
"Canadian Application Serial No. 2,585,862, Response filed May 7, 2013 to Office Action dated Nov. 21, 2012", 16 pgs.
"Canadian Application Serial No. 2,585,862, Response filed Jun. 13, 2012 to Office Action dated Mar. 21, 2012", 7 pgs.
"Canadian Application Serial No. 2,734,293, Office Action dated Oct. 28, 2015", 4 pgs.
"Canadian Application Serial No. 2,734,293, Response filed Apr. 25, 2016 to Office Action dated Oct. 28, 2015", 19 pgs.
"Canadian Application Serial No. 2,780,063, Office Action dated Jan. 20, 2017", 4 pgs.
"Canadian Application Serial No. 2,780,063, Office Action dated Apr. 4, 2016", 5 pgs.
"Canadian Application Serial No. 2,780,063, Response filed Jul. 19, 2017 to Office Action dated Jan. 20, 2017", 8 pgs.
"Canadian Application Serial No. 2,780,063, Response filed Oct. 3, 2016 to Office Action dated Apr. 4, 2016", 15 pgs.
"Canadian Application Serial No. 2,866,539, Office Action dated Mar. 29, 2018", 4 pgs.
"Canadian Application Serial No. 2,877,645, Office Action dated Feb. 12, 2016", 6 pgs.
"Canadian Application Serial No. 2,877,645, Response filed Aug. 12, 2016 to Office Action dated Feb. 12, 2016", 21 pgs.
"Chinese Application Serial No. 201080060338.6, Amendment filed May 17, 2013", w/English Claims, 10 pgs.
"Chinese Application Serial No. 201080060338.6, Office Action dated Jun. 13, 2014", w/English Translation, 24 pgs.
"Chinese Application Serial No. 201380024117.7, Office Action dated Mar. 3, 2016", (English Translation), 8 pgs.
"Chinese Application Serial No. 201380024117.7, Response filed Jul. 15, 2016 to Office Action dated Mar. 3, 2016", (English Translation of Claims), 10 pgs.
"Chinese Application Serial No. 201380024117.7, Voluntary Amendment filed Apr. 17, 2015", (English Translation of Claims), 9 pgs.
"Chinese Application Serial No. 201680031145.5, Office Action dated Mar. 18, 2020", w/English Translation, 10 pgs.
"European Application Serial No. 05712204.6, Office Action dated Oct. 8, 2010", 7 pgs.
"European Application Serial No. 05712204.6, Office Action dated Oct. 24, 2006", 2 pgs.
"European Application Serial No. 05712204.6, Response filed Jan. 14, 2011 to Office Action dated Oct. 8, 2010", 18 pgs.
"European Application Serial No. 05712204.6, Response filed Nov. 9, 2006 to Office Action dated Oct. 24, 2006", 1 pg.
"European Application Serial No. 05712204.6, Supplementary European Search Report dated Dec. 18, 2008", 3 pgs.
"European Application Serial No. 05793736.9, European Search Report dated Jan. 7, 2008", 6 pgs.
"European Application Serial No. 05793736.9, Office Action dated Jul. 14, 2008", 1 pg.
"European Application Serial No. 05793736.9, Response filed Nov. 24, 2008 to Office Action dated Jul. 14, 2008", 11 pgs.
"European Application Serial No. 09808836.2, Communication Pursuant to Article 94(3) EPC dated Nov. 11, 2015", 5 pgs.
"European Application Serial No. 09808836.2, Extended European Search Report dated Apr. 1, 2014", 6 pgs.
"European Application Serial No. 09808836.2, Intention to Grant dated Jul. 13, 2016", 85 pgs.

(56) References Cited

OTHER PUBLICATIONS

"European Application Serial No. 09808836,2, Office Action dated May 24, 2011", 2 pgs.
"European Application Serial No. 09808836,2, Response filed Mar. 17, 2016 to Communication Pursuant to Article 94(3) EPC dated Nov. 11, 2015", 8 pgs.
"European Application Serial No. 09808836.2, Response filed Oct. 24, 2014 to Extended European Search Report dated Apr. 1, 2014", 9 pgs.
"European Application Serial No. 09824192.0, Extended European Search Report dated Mar. 21, 2014", 7 pgs.
"European Application Serial No. 09824192.0, Response filed Oct. 20, 2014 to Extended European Search Report dated Mar. 21, 2014", 18 pgs.
"European Application Serial No. 10825339.4, Extended European Search Report dated Jun. 18, 2014", 6 pgs.
"European Application Serial No. 10827286.5, Extended European Search Report dated Jun. 24, 2014", 4 pgs.
"European Application Serial No. 10827286.5, Office Action dated Jun. 14, 2012", 2 pgs.
"European Application Serial No. 10827286.5, Response filed Dec. 19, 2012 to Office Action dated Jun. 14, 2012", 9 pgs.
"European Application Serial No. 12006956.2, Examination Notification Art. 94(3) dated Apr. 14, 2014", 6 pgs.
"European Application Serial No. 12006956.2, Extended European Search Report dated May 22, 2013", 8 pgs.
"European Application Serial No. 12006956.2, Invitation to Remedy Deficiencies dated Nov. 9, 2012", 4 pgs.
"European Application Serial No. 12006956.2, Response filed Nov. 26, 2012 to Invitation to Remedy Deficiencies dated Nov. 9, 2012", 7 pgs.
"European Application Serial No. 12006956.2, Response filed Dec. 19, 2013 to Extended European Search Report dated May 22, 2013", 7 pgs.
"European Application Serial No. 12006956.2, Summons to Attend Oral Proceedings mailed May 13, 2015", 10 pgs.
"European Application Serial No. 13711520.0, Examination Notification Art. 94(3) dated Jan. 4, 2016", 5 pgs.
"European Application Serial No. 13711520.0, Intention to Grant dated Jul. 5, 2016", 5 pgs.
"European Application Serial No. 13711520.0, Office Action dated Nov. 20, 2014", 2 pgs.
"European Application Serial No. 13711520.0, Response filed Jun. 1, 2015 to Office Action dated Nov. 20, 2014", 11 pgs.
"European Application Serial No. 16728195.5, Response filed Jul. 19, 2018 to Office Action dated Jan. 25, 2018", 10 pgs.
"European Application Serial No. 200901078, Office Action dated Jul. 10, 2012", 2 pgs.
"European Application Serial No. 200901078, Response filed Jan. 17, 2013 to Office Action dated Jul. 10, 2012", 10 pgs.
"International Application Serial No. PCT/EP2004/011481, International Search Report dated Sep. 2, 2005", 3 pgs.
"International Application Serial No. PCT/US2005/002670, International Written Opinion dated Jun. 28, 2006", 3 pgs.
"International Application Serial No. PCT/US2005/031127, International Written Opinion dated Sep. 26, 2006", 3 pgs.
"International Application Serial No. PCT/US2006/022428, International Preliminary Report on Patentability dated Dec. 11, 2007", 4 pgs.
"International Application Serial No. PCT/US2006/022428, International Search Report dated Oct. 26, 2007", 1 pg.
"International Application Serial No. PCT/US2006/022428, Written Opinion dated Oct. 26, 2007", 3 pgs.
"International Application Serial No. PCT/US2009/054518, International Preliminary Report on Patentability dated Feb. 22, 2011", 9 pgs.
"International Application Serial No. PCT/US2009/054518, International Search Report dated Oct. 15, 2009", 2 pgs.
"International Application Serial No. PCT/US2009/054518, Written Opinion dated Oct. 15, 2009", 8 pgs.
"International Application Serial No. PCT/US2009/062846, International Preliminary Report on Patentability dated May 3, 2011", 9 pgs.
"International Application Serial No. PCT/US2009/062846, International Search Report dated Jan. 13, 2010", 4 pgs.
"International Application Serial No. PCT/US2009/062846, Written Opinion dated Jan. 13, 2010", 8 pgs.
"International Application Serial No. PCT/US2009/063015, International Preliminary Report on Patentability dated May 8, 2012", 6 pgs.
"International Application Serial No. PCT/US2009/063015, International Search Report dated Jul. 27, 2010", 4 pgs.
"International Application Serial No. PCT/US2009/063015, Written Opinion dated Jul. 27, 2010", 5 pgs.
"International Application Serial No. PCT/US20091061941, International Search Report dated Dec. 18, 2009", 1 pg.
"International Application Serial No. PCT/US2010/028729, International Preliminary Report on Patentability dated Jul. 23, 2012", 17 pgs.
"International Application Serial No. PCT/US2010/028729, International Search Report dated Jan. 10, 2011", 3 pgs.
"International Application Serial No. PCT/US2010/028729, Written Opinion dated Jan. 10, 2011", 4 pgs.
"International Application Serial No. PCT/US2010/030524, International Preliminary Report on Patentability dated Apr. 24, 2012", 1 pg.
"International Application Serial No. PCT/US2010/030524, International Search Report dated Jun. 10, 2010", 3 pgs.
"International Application Serial No. PCT/US2010/030524, Written Opinion dated Jun. 10, 2010", 13 pgs.
"International Application Serial No. PCT/US2011/023189, International Preliminary Report on Patentability dated Aug. 1, 2013", 7 pgs.
"International Application Serial No. PCT/US2011/023189, International Search Report dated Feb. 17, 2012", 4 pgs.
"International Application Serial No. PCT/US2011/031980, International Preliminary Report on Patentability dated Oct. 18, 2012", 8 pgs.
"International Application Serial No. PCT/US2011/031980, International Search Report dated Jun. 28, 2011", 3 pgs.
"International Application Serial No. PCT/US2013/029767, International Preliminary Report on Patentability dated Sep. 18, 2014", 9 pgs.
"International Application Serial No. PCT/US2013/029767, International Search Report dated Jun. 14, 2013", 6 pgs.
"International Application Serial No. PCT/US2013/029767, Written Opinion dated Jun. 14, 2013", 7 pgs.
"International Application Serial No. PCT/US2016/034719, International Preliminary Report on Patentability dated Dec. 7, 2017", 10 pgs.
"International Application Serial No. PCT/US2016/034719, International Search Report dated Oct. 17, 2016", 7 pgs.
"International Application Serial No. PCT/US2016/034719, Invitation to Pay Additional Fees and Partial Search Report dated Aug. 11, 2016", 6 pgs.
"International Application Serial No. PCT/US2016/034719, Written Opinion dated Oct. 17, 2016", 8 pgs.
"Japanese Application Serial No. 2007-538901, Office Action dated Jan. 20, 2010", (W/ English Translation), 9 pgs.
"Japanese Application Serial No. 2007-538901, Response filed Jul. 20, 2010 to Office Action dated Jan. 20, 2010", (W/ English Translation), 16 pgs.
"Japanese Application Serial No. 2011-524007, Office Action dated Mar. 19, 2014", w/English Translation, 6 pgs.
"Japanese Application Serial No. 2011-524007, Office Action dated Aug. 29, 2013", w/English Translation, 8 pgs.
"Japanese Application Serial No. 2011-524007, Response filed Oct. 30, 2013 to Office Action dated Aug. 29, 2013", w/English Translation, 13 pgs.
"Japanese Application Serial No. 2011-524007, Voluntary Amendment filed Aug. 29, 2012", W/English Claims, 8 pgs.

(56) References Cited

OTHER PUBLICATIONS

"Japanese Application Serial No. 2017-561840, Notification of Reasons for Rejection dated Apr. 22, 2020", with English translation, 9 pages,.

"Knee Implant Surgery Techniques Can Obscure Tech Advances-NIH Panel", FDC Reports, The Gray Sheet, (Dec. 15, 2003), 1 pg.

"Knee Implant Wear Debris, Changing Demographics Weighed by NIH Panel", FDC Reports, The Gray Sheet, (Dec. 1, 2003), 1 pg.

"Korean Application Serial No. 10-2007-7011837, Office Action dated Jun. 22, 2011", 4 pgs.

"Korean Application Serial No. 1020067018160, Request for Substantive Examination and Amendment filed Dec. 4, 2009", w/English claims, 29 pgs.

"New Zealand Application Serial No. 201001389, Response filed Mar. 19, 2013 to Office Action dated Mar. 21, 2012", 21 pgs.

"New Zealand Application Serial No. 591206, Examiner Report dated Apr. 4, 2013", 2 pgs.

"New Zealand Application Serial No. 591206, Examiner Report dated Mar. 21, 2012", 2 pgs.

"New Zealand Application Serial No. 591206, Response filed Jun. 13, 2013 to Examiner Report dated Apr. 4, 2013", 10 pgs.

"NIH Consensus: More Knee Replacements Among Young, Old to Grow Market", FDC Reports, The Gray Sheet, (Dec. 15, 2003), 1 pg.

Albee, Fred H, "Bone Surgery With Machine Tools", Scientific American vol. 154.4, (Apr. 1936), 178-181.

Delio, Michelle, "Hoping for a Knee-Jerk Reaction", Wired News, [Online], Retrieved from the internet: <http://wiredvig.wired.com/news/medtech/0,1286,62716,00.html?tw-newsletter_to>, (2004), 3 pgs.

Eckhoff, D. G, et al., "Three-Dimensional Morphology and Kinematics of the Distal Part of the Femur Viewed in Virtual Reality", Journal of Bone & Joint Surgery, vol. 85-A, Supplement 4, (2003), 97-104.

Howe, Robert D, et al., "Robotics for Surgery", Annual Rev. Biomed. Eng., (1999), 211-240.

Mihalko, W. H, et al., "Comparison of Ligament-Balancing Techniques During Total Knee Arthroplasty", Journal of Bone & Joint Surgery, vol. 85-A, Supplement 4,, (2003), 132-135.

Murray, D. G, et al., "Variable Axis Total Knee Surgical Technique", Howmedica Surgical Techniques, Howmedica, Inc., (1977), 2-7.

Palmer, et al., "Total Knee Arthoplasty", [Online], Retrieved from the internet: <http://www.emedicine.com/orthoped/topic347.htm.>, (2003), 18 pgs.

Rapp, "Electronic Knee implant May Benefit Future TKR Patients", Orthopedics Today, vol. 25, No. 3, (Mar. 2005), 14-15.

Ries, et al., "Soft-Tissue Balance in Revision Total Knee Arthroplasty", Jnl. Bone & Jt. Surg., vol. 86-A Supplement 1, (2003), 82-86.

Ries, M. D, et al., "Soft-Tissue Balance in Revision Total Knee Arthroplasty", Journal of Bene & Joint Surgery, vol. 85-A, Supplement 4,, (2003), 38-42.

Stryker, "Precision Oscillating Tip Saw—Ref 6209, Instruction for Use", 6209-001-708 Rev-A, (2006), 21 pgs.

Stryker, "Precision Oscillating Tip Saw [pamphlet]", Literature No. MTX9100001044, (2006), 2 pgs.

Synvasive Technology Inc, "Achieve Dynamic Balance—Improve your demanding patient's post-op stability", 2005 Annual Meeting of Orthopedic Surgeons (Washington DC), (2005), 2 pgs.

"Canadian Application Serial No. 2,985,705, Office Action dated Feb. 4, 2021", 3 pgs.

"Canadian Application Serial No. 2,985,705, Office Action dated Sep. 24, 2021", 4 pgs.

"Canadian Application Serial No. 2,985,705, Response filed Jun. 3, 2021 to Office Action dated Feb. 4, 2021", 51 pgs.

KNEE BALANCING DEVICES, SYSTEMS AND METHODS

CLAIM OF PRIORITY

This patent application is a continuation of U.S. patent application Ser. No. 13/659,280, filed on Oct. 24, 2012, which claims the benefit of priority under 35 U.S.C. § 119(e) to U.S. Provisional Patent Application Ser. No. 61/550,766, entitled "KNEE BALANCING SYSTEM AND METHOD," filed on Oct. 24, 2011, each of which are hereby incorporated by reference in its entirety.

TECHNICAL FIELD

This patent document relates generally to surgical devices, systems and methods. More specifically, but not by way of limitation, this patent document relates to devices, systems and methods for facilitating knee surgical procedures, such as knee replacement procedures.

BACKGROUND

Knee arthritis is a debilitating problem that is increasing in prevalence due to an aging population and an obesity epidemic in much of the world. In an arthritic knee, protective cartilage at a point of articulation between a femur and a tibia is often worn away, diseased or otherwise damaged, causing significant pain, discomfort, and disability for a human subject. In many cases, knee arthritis leads human subjects to seek knee replacement surgery, also referred as "knee arthroplasty." Nearly 600,000 knee replacement surgeries are performed annually in the U.S. alone.

Knee arthroplasty involves replacing one or more worn, diseased or otherwise damaged knee joint surfaces with metal and/or plastic components shaped to allow natural motion of the knee. Knee replacement can be total or partial. Total knee replacement surgery, also referred to as total knee arthroplasty ("TKA"), involves a total replacement of a distal end of a femur, a proximal end of a tibia, and often an inner surface of a patella with prosthetic parts. Cuts are made on the distal end of the femur, the proximal end of the tibia, and optionally, the inner surface of the patella. Prosthetic parts are then attached to the cut surfaces. The prosthetic parts are intended to create a stable knee joint that moves through a normal range of motion. The replacement of knee structures with prosthetic parts can, if appropriately implanted, allow the knee to avoid bone-on-bone contact and provide smooth, well-aligned surfaces for joint movement.

OVERVIEW

The present inventors recognize, among other things, that one of the most important aspects of a successful TKA procedure is ensuring that ligament or soft tissue tension is balanced on both sides of a knee joint. Four ligaments can be important in the proper functioning of a knee—the anterior cruciate ligament, the posterior cruciate ligament, the medial collateral ligament, and the lateral collateral ligament. Ideally, there should be approximately equal ligament or soft tissue tension on a medial side of the knee joint and on a lateral side of the knee joint once the prosthetic knee is implanted. If there is ligament or soft tissue imbalance, the prosthetic knee will often not work properly, not feel right, and/or wear unevenly, potentially resulting in another knee replacement in just a few years' time. Typically, ligament or soft tissue balancing during a TKA procedure is done through approximation by an attending surgeon or other caregiver, often using multiple shims inserted between the distal femur and proximal tibia during the procedure to approximate an ideal tension balance. Such approximations require a great deal of experience and skill, and if done improperly, the results of the TKA procedure can be significantly compromised.

As such, the present inventors recognize that there is a need for devices, systems and methods configured to facilitate knee balancing during a TKA procedure, for example. The devices, systems and methods can be configured to help an attending surgeon or other caregiver estimate ligament or soft tissue tension on medial and lateral sides of the knee so that ligament release(s) can be performed as necessary. The devices, systems and methods can be configured to be relatively simple to use and nonintrusive upon the rest of the TKA procedure.

Devices, systems and methods are provided for facilitating knee balancing during a knee replacement surgery. A system can include a force sensor, a main body, a moveable sensor platform, and an adjustment mechanism. The force sensor can sense one or more forces applied within a knee joint, including forces applied on a medial side and a lateral side. The movable sensor platform can be coupled between the force sensor and the main body. The adjustment mechanism can adjust the moveable sensor platform, relative to the main body, thereby adjusting a collective height of the system. A method can include inserting portions of a knee balancing system into a gap formed between a distal end of a femur and a proximal end of a tibia, adjusting an adjustable mechanism of the knee balancing system to increase or decrease a collective height of the system, and sensing and displaying the medial and lateral forces.

To better illustrate the knee balancing devices, systems and methods disclosed herein, a non-limiting list of examples is provided here:

In Example 1, a knee balancing system for facilitating a knee arthroplasty procedure comprises a force sensor configured to sense one or more forces applied within a knee joint, including a force applied on a medial side of the knee joint and a force applied on a lateral side of the knee joint; a main body; a moveable sensor platform, coupled between the force sensor and the main body; and an adjustment mechanism configured to adjust the moveable sensor platform relative to the main body.

In Example 2, the system of claim 1 is optionally configured such that the force sensor is configured to sense one or more forces applied within the knee joint between a cut distal end of a femur and a cut proximal end of a tibia.

In Example 3, the system of any one or any combination of Examples 1 or 2 optionally further comprises a numerical display, wirelessly or integrally coupled with the force sensor, configured to display a first number representing the force applied on the medial side and a second number representing the force applied on the lateral side.

In Example 4, the system of any one or any combination of Examples 1-3 is optionally configured such that movement of the adjustment mechanism results in the moveable sensor platform moving up or down, relative to the main body, to respectively increase or decrease a height of portions of the force sensor that reside within the knee joint, relative to the main body.

In Example 5, the system of Example 4 is optionally configured such that a collective height of portions of the force sensor, the main body, the moveable sensor platform, and the adjustable mechanism that reside within the knee joint is adjustable from about 15 millimeters to about 21 millimeters.

In Example 6, the system of any one or any combination of Examples 1-5 is optionally configured such that one or both of the movable sensor platform or the adjustment mechanism includes a plurality of height markings.

In Example 7, the system of any one or any combination of Examples 1-6 is optionally configured such that the main body includes a platform configured to be inserted into the knee joint and couple with the moveable sensor platform; a shaft extending from the platform; and a handle at an end of the shaft, opposite the platform.

In Example 8, the system of Example 7 is optionally configured such that the shaft extends from a location that is offset from a center of the platform.

In Example 9, the system of any one or any combination of Examples 1-8 is optionally configured such that the adjustment mechanism includes one or more threaded screws or bolts.

In Example 10, the system of Example 9 is optionally configured such that the adjustment mechanism further includes an adjustable wedge movable within a perimeter of the main body through rotation of the one or more threaded screws or bolts.

In Example 11, the system of Example 10 is optionally configured such that the adjustable wedge includes a base member, one or more plate members, and one or more column members, the one or more plate members are moveable within the perimeter of the main body through rotation of the one or more threaded screws or bolts.

In Example 12, the system of Example 11 is optionally configured such that the one or more column members move along a first planar direction when the one or more plate members move along a second planar direction, which is perpendicular to the first planar direction.

In Example 13, the system of any one or any combination of Examples 9-12 is optionally configured such that the adjustment member further includes a screwdriver or a wrench.

In Example 14, the system of any one or any combination of Examples 1-13 is optionally configured such that the adjustment mechanism includes one or more actuating ramped surfaces configured to adjust the moveable sensor platform relative to the main body.

In Example 15, the system of Example 14 is optionally configured such that the moveable sensor platform includes one or more actuating ramped surfaces that engage with the one or more actuating ramped surfaces of the adjustment mechanism.

In Example 16, a method for facilitating balancing tension applied to a knee joint by one or more ligaments or other soft tissue during a knee arthroplasty procedure comprises inserting portions of a knee balancing system, including a force sensor, a main body, a movable sensor platform coupled between the force sensor and the main body, and an adjustment mechanism, into a gap formed between a distal end of a femur and a proximal end of a tibia; adjusting the adjustable mechanism of the knee balancing system to increase or decrease a collective height of the system, including moving the moveable sensor platform and the force sensor relative to the main body; sensing, using the force sensor, an amount of medial force applied against a medial portion of the knee balancing system by the femur and the tibia and an amount of lateral force applied against a lateral portion of the knee balancing system by the femur and the tibia; and displaying the amounts of medial and lateral force on the knee balancing system.

In Example 17, the method of Example 16 optionally further comprises releasing at least one ligament or soft tissue structure of the knee joint based on the displayed amounts of medial and lateral force.

In Example 18, the method of any one or any combination of Examples 16 or 17 is optionally configured such that inserting the portions of the knee balancing system into the gap formed between the distal end of the femur and the proximal end of the tibia includes inserting the portions of the knee balancing system between a cut surface of the distal end of the femur and a cut surface of the proximal end of the tibia.

In Example 19, the method of any one or any combination of Examples 16-18 is optionally configured such that adjusting the adjustable mechanism of the knee balancing system includes increasing the collective height of the system from about 15 millimeters to at least about 17 millimeters.

In Example 20, the method of any one or any combination or Examples 16-19 is optionally configured such that adjusting the adjustable mechanism of the knee balancing system includes engaging one or more threads of a screw or a bolt with an adjustable wedge including one or more actuating ramped surfaces.

In Example 21, the method of Example 20 is optionally configured such that engaging the one or more threads of the screw or the bolt with the adjustable wedge includes turning a wrench or a screwdriver coupled with the screw or bolt.

In Example 22, the method of any one or any combination of Examples 16-21 is optionally configured such that adjusting the adjustable mechanism of the knee balancing system includes engaging one or more threads of a first screw or first bolt with a first plate member and engaging one or more threads of a second screw or second bolt with a second plate member.

In Example 23, the method of Example 22 is optionally configured such that engaging the one or more threads of the first screw or first bolt with the first plate member includes adjusting the collective height of the medial portion of the knee balancing system, and wherein engaging the one or more threads of the second screw or second bolt with the second plate member includes adjusting the collective height of the lateral portion of the knee balancing system.

In Example 24, the method of any one or any combination of Examples 16-23 is optionally configured such that displaying the amounts of medial and lateral force includes displaying a first numerical value representing an amount of force applied against the medial portion of the knee balancing system and a second numerical value representing an amount of force applied against the lateral portion of the knee balancing system.

In Example 25, the knee balancing device, system, or method of any one (or portion or one) or any combination of Examples 1-24 is optionally configured such that all elements or options recited are available to use or select from.

These and other examples and features of the present knee balancing devices, systems, or methods will be set forth in part in the following Detailed Description. This Overview is intended to provide non-limiting examples of the present subject matter—it is not intended to provide an exclusive or exhaustive explanation. The Detailed Description below is included to provide further information about the present knee balancing devices, systems and methods.

BRIEF DESCRIPTION OF THE DRAWINGS

In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present document.

DETAILED DESCRIPTION

The present inventors recognize that there is a need for devices, systems and methods configured to facilitate knee balancing during a TKA procedure, as well as other procedures that can benefit through distraction from a thin profile. The devices, systems and methods can be configured to help an attending surgeon or other caregiver estimate ligament or soft tissue tension on medial and lateral sides of a knee, and optionally, the anterior and posterior sides of the knee so that appropriate ligament release(s) can be performed. In this way, a prosthetic knee joint can be more optimally implanted. The devices, systems and methods can be configured to be relatively simple to use and nonintrusive upon the rest of the TKA procedure.

Figure 1:
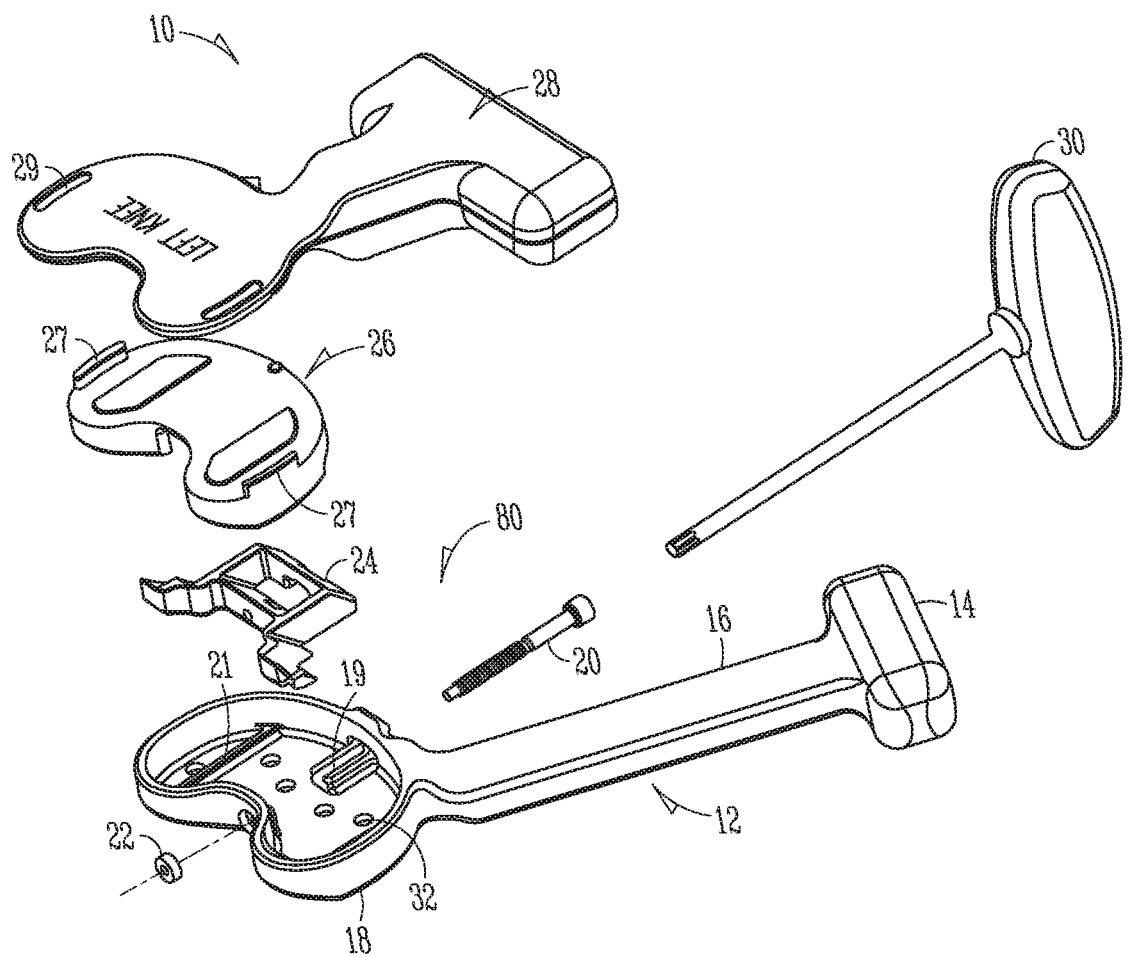
FIG. 1: illustrates an exploded view of a knee balancing system, as constructed in accordance with at least one embodiment.

FIG. 1 illustrates an example of a knee balancing system 10, as constructed in accordance with at least one embodiment of the present disclosure. The knee balancing system 10 can include a main body (or "stationary member") 12, an adjustable wedge 24, a force sensor 28, a moveable sensor platform 26 coupled between the force sensor 28 and the main body 12, and an adjustment wrench 30. The moveable sensor platform 26 can include one or more attachment members 27 for attaching with mating attachment members (e.g., voids) 29 on the force sensor 28.

Optionally, one or more of the knee balancing system 10 components can be sterilized, such as by autoclave, chemical sterilization, or the like, and thereafter reused. In varying examples, all components of the system 10 except the force sensor 28 can be sterilized and reused. It can be advantageous for patient safety to have the force sensor 28 configured as a disposable component of the system 10. To this end, the attachment members 27, 29 can be keyed to "talk" to each other (e.g., via a mechanical attachment mechanism, an electronic recognition system, or some combination of the two) enabling the system 10 to be configured such that no other force sensor, other than the force sensor 28 provided with the system 10, can be used. This prevents the use of inferior and potentially dangerous counterfeit, worn out, or insufficiently sterilized force sensors from being used. As an alternative to the attachment members 27, 29 talking to each other, the force sensor 28 can be programmed to work in one surgical procedure only and thereafter be permanently shut down or disabled.

The main body 12 can include a handle 14, a shaft 16, and a platform 18. The main body 12 can be made of any suitable material, such as but not limited to stainless steel, other metals, or polymers. In some examples, the platform 18 can include one or more drainage holes 32 to facilitate cleaning of the main body 12 and/or a general shape approximating a knee joint surface on which it is to be placed. The shaft 16, which extends from the platform 18, can be offset from the center of the platform 18. This offset configuration can facilitate inserting the platform 18 into a knee joint when the patella is moved off to one side of the joint. It can also facilitate adjusting the system 10 by leaving more room for accessing an adjustment screw 20. The handle 14 can have any suitable configuration for enhancing ergonomics and ease of use of the main body 12.

The platform 18 can include a track 19 and one or more guide rails 21. The adjustable wedge 24 can be attached to the platform 18, such as via the adjustment screw 20 and an adjustment screw capture nut 22, to ride over the track 19 and one or more guide rails 21. In this example, an adjustment mechanism 80 can include one or more of the adjustable wedge 24, the adjustment screw 20, the adjustment screw capture nut 22, and the adjustment wrench 30. The adjustment mechanism 80 can be configured to adjust the moveable sensor platform 26, relative to the main body 12, thereby adjusting a collective height of the system 10 (i.e., a distance from a surface of the system engagable with a cut distal femur to a surface of the system engagable with a cut proximal tibia).

When assembled, portions of the knee balancing system 10 can be advanced into a gap between the cut distal femur and the cut proximal tibia during knee replacement surgery. The adjustment wrench 30 can be used to adjust the collective height (or "thickness") of the system 10 portions residing in the gap. The collective height of the system 10 portions residing in the gap can, in some examples, range between about 15 millimeters and about 21 millimeters, inclusive. The collective height can be about 15 millimeters for insertion into the gap and, when fully expanded, be about 21 millimeters. As the collective height of the system 10 increases, the force sensor 28 can be used to sense forces applied by a medial part of the knee and a lateral part of the knee. Ligament release(s) can then be performed, if necessary, to balance the medial and lateral forces, after which time the system 10 can be removed and the knee replacement procedure completed.

Figure 2:
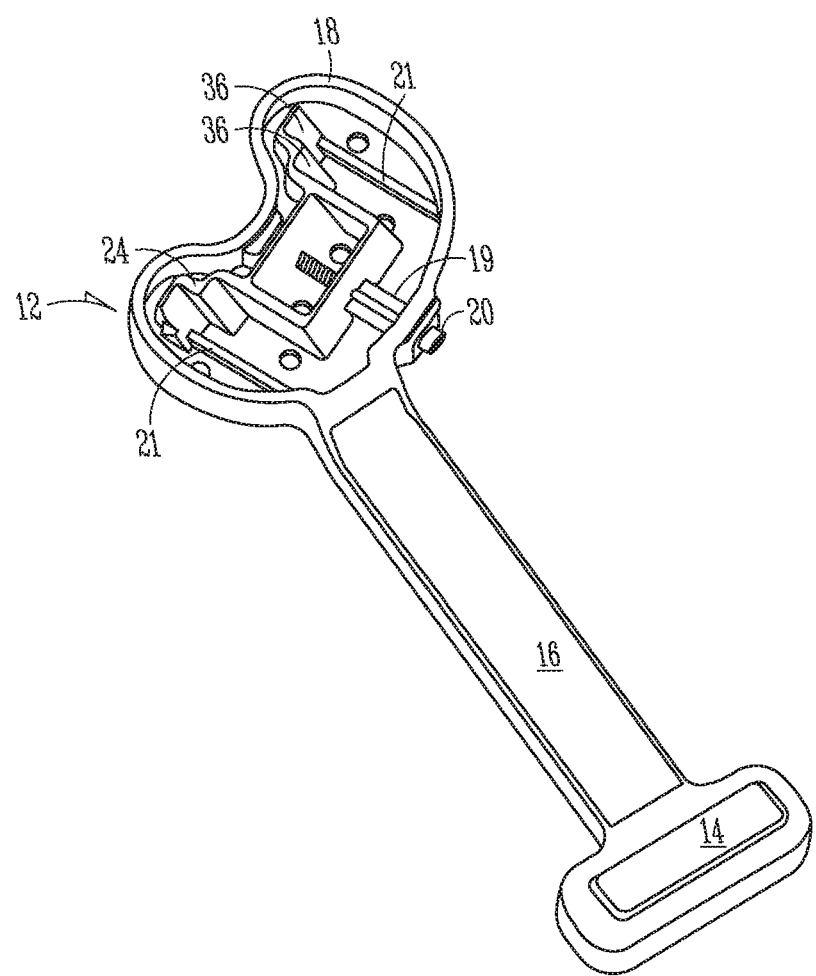
FIG. 2: illustrates an elevation view of a bottom side of a main body and an adjustment mechanism of a knee balancing system, as constructed in accordance with at least one embodiment.

FIG. 2 illustrates an elevation view of a bottom side of the main body 12 and the adjustable wedge 24. The adjustable wedge 24 is shown in place within the main body 12 and is attached via the adjustment screw 20. When the adjustment screw 20 is operated, the adjustable wedge 24 can move backward and/or forward within a perimeter of the platform 18, guided by the one or more guide rails 21 and the track 19.

Figure 3:
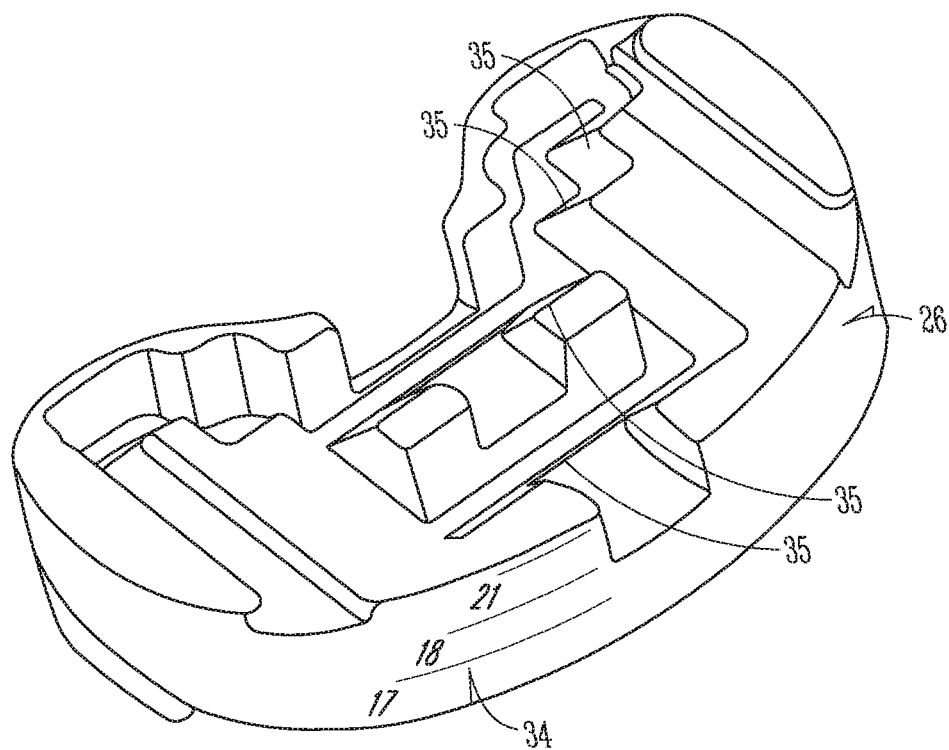
FIG. 3: illustrates an elevation view of a top side of a movable sensor platform of a knee balancing system, as constructed in accordance with at least one embodiment.

FIG. 3 illustrates an elevation view of a top side of the moveable sensor platform 26. As shown, the moveable sensor platform can have a general outer shape similar to that of the platform 18. The moveable sensor platform 26 can include graduated distraction height markings 34, such as on an outer surface, to indicate to an attending surgeon or other caregiver a current height of the gap between a patient's cut distal femur and cut proximal tibia. The height can, in some examples, be measured in increments of about 2 mm, from about 15 mm fully collapsed to about 21 mm when fully expanded. In alternative examples, other markings can be included on the moveable sensor platform 26, such as 1 mm incremental markings, various colored dots or lines with or without numbers, colored stripes or the like or, as shown in FIG. 5B, markings 34A can be included on a column member of an adjustment mechanism.

The moveable sensor platform 26 can include one or more actuating ramped surfaces 35 to mate with corresponding actuating ramped surfaces 36 (FIG. 2) on the adjustable wedge 24. By coupling the moveable sensor platform 26 between the adjustable wedge 24 (FIG. 1) and the force sensor 28 (FIG. 1), the moveable sensor platform 26 can adjust the collective height of the system 10 portions that fit into the gap between the cut distal femur and the cut proximal tibia. Optionally, the force sensor 28 and the moveable sensor platform 26 can be combined as a single piece.

Figure 4:
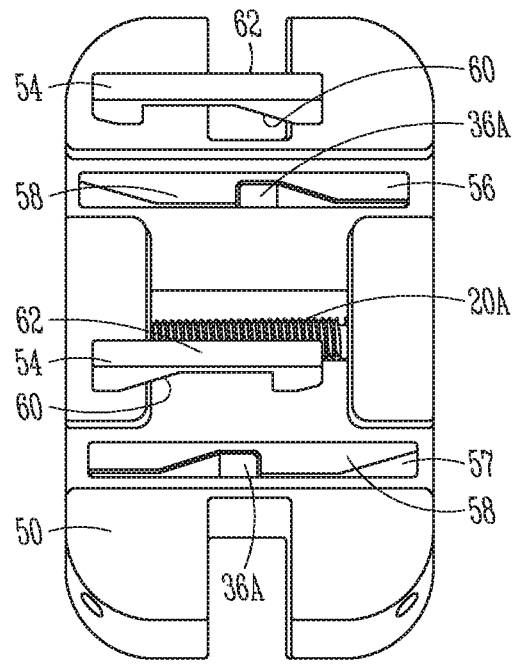
FIGS. 4, 7, 10, and 13: illustrate an elevation exploded view of a bottom side of portions of an adjustment mechanism of a knee balancing system, as constructed in accordance with various embodiments.
Figure 5A:
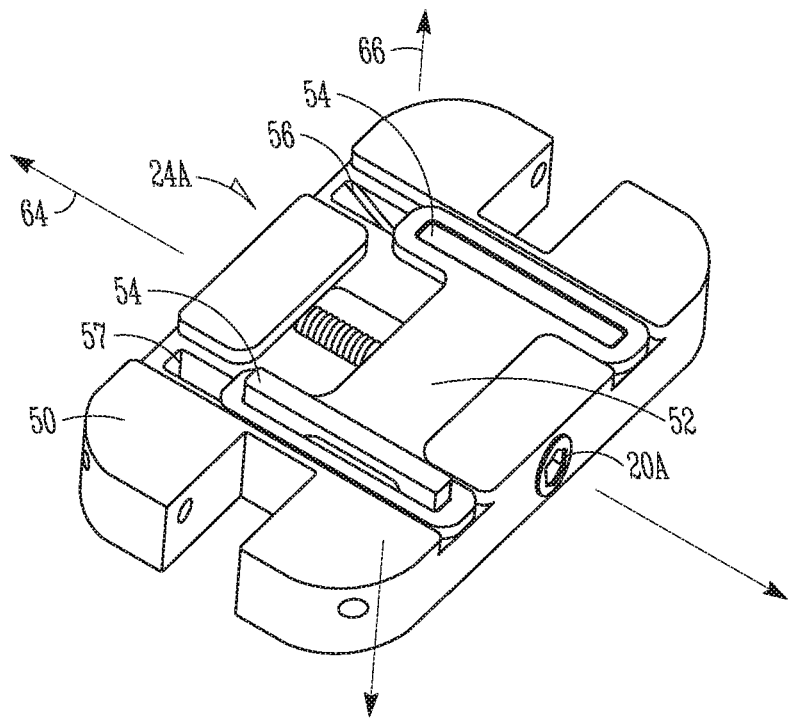
FIGS. 5A-5B, 8A-8B, 11, and 14: illustrate an elevation view of a bottom side of an adjustment mechanism of a knee balancing system, as constructed in accordance with various embodiments.
Figure 5B:
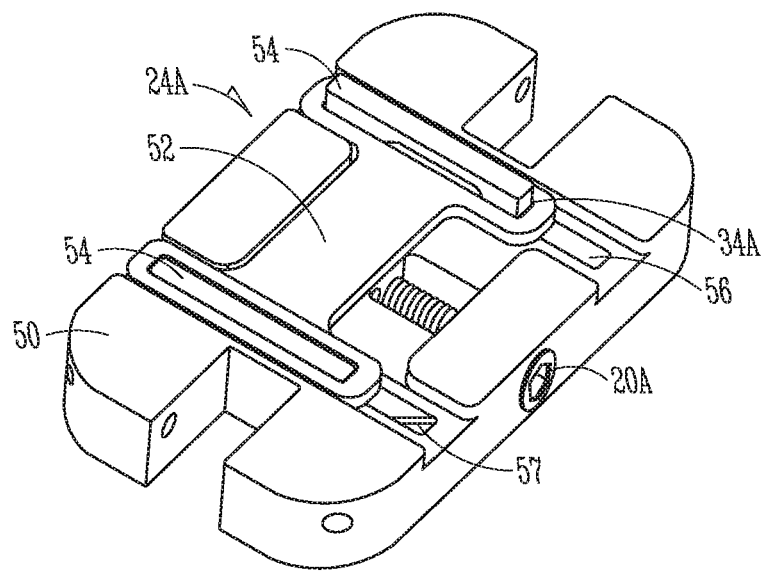
Figure 6:
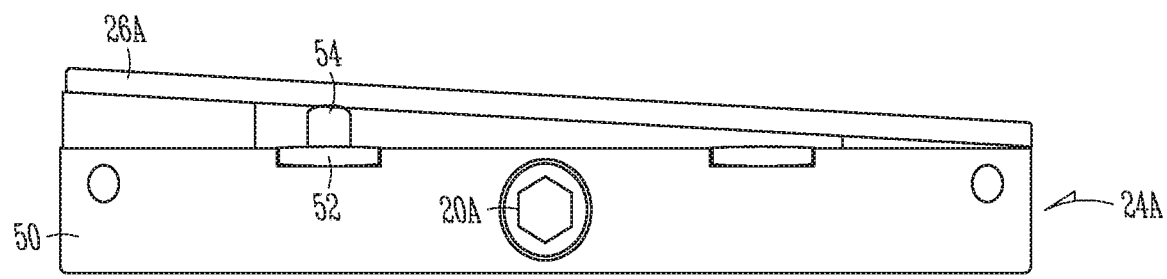
FIGS. 6, 9, 12, and 15: illustrate a front assembled view of an adjustment mechanism and a movable sensor platform, as constructed in accordance with various embodiments.
Figure 7:
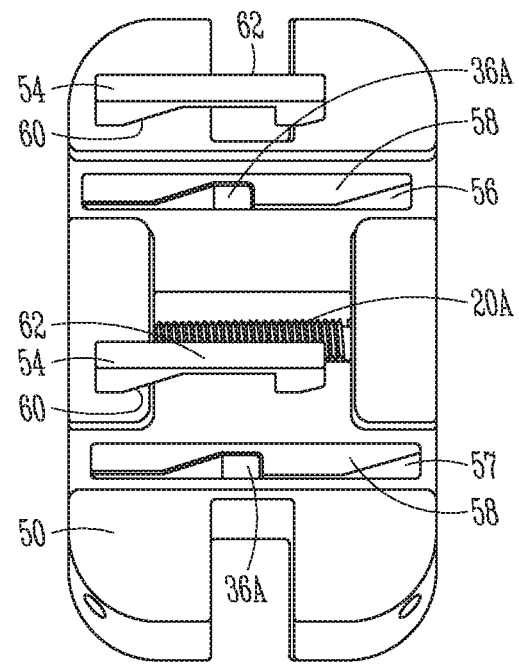
Figure 8A:
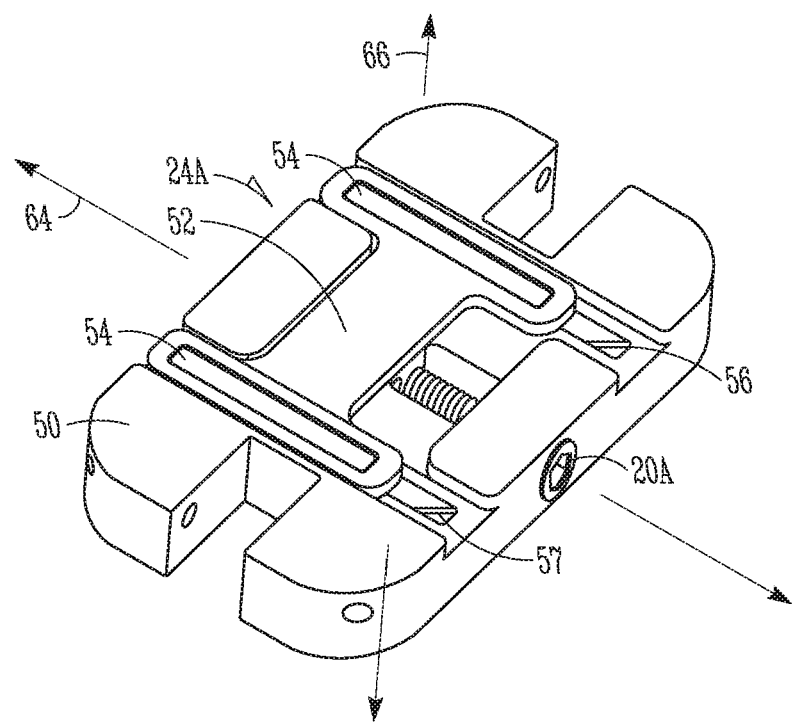
Figure 8B:
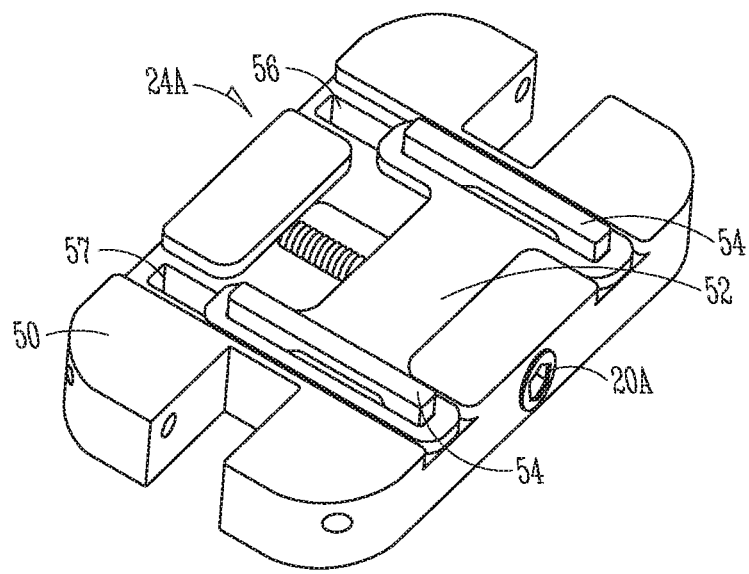
Figure 9:
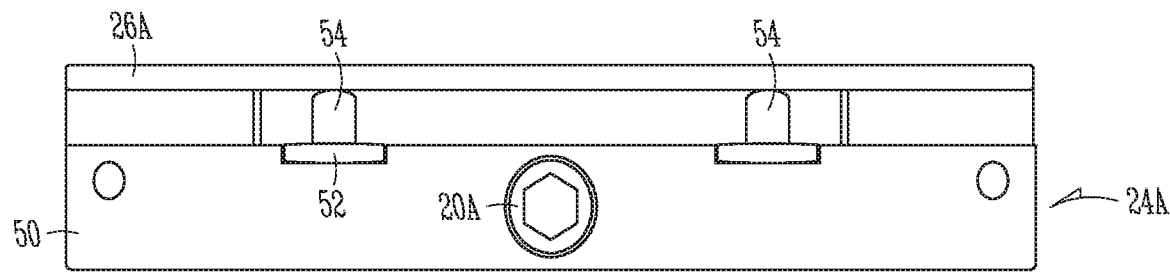
Figure 10:
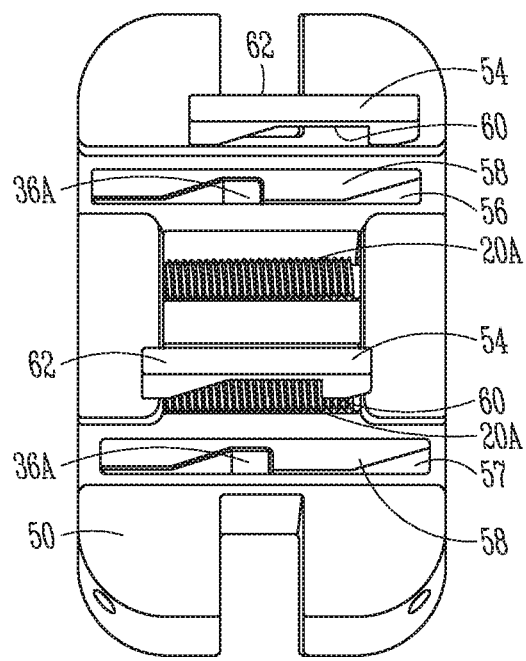
Figure 11:
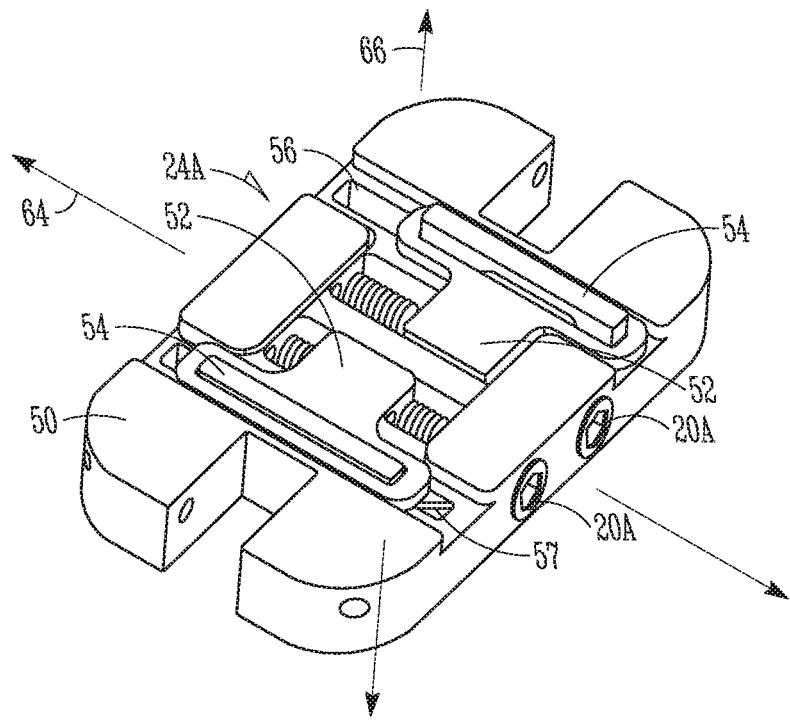
Figure 12:
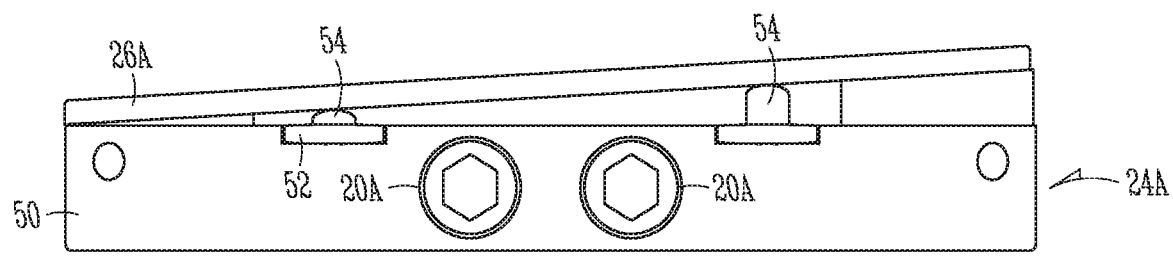
Figure 13:
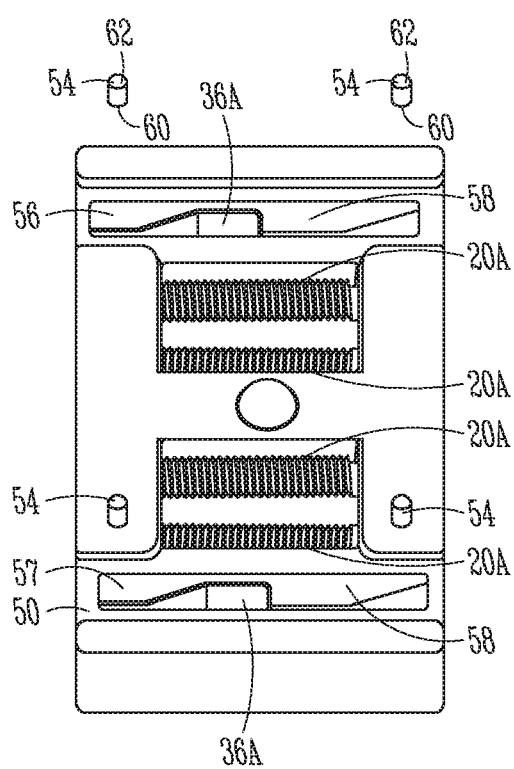
Figure 14:
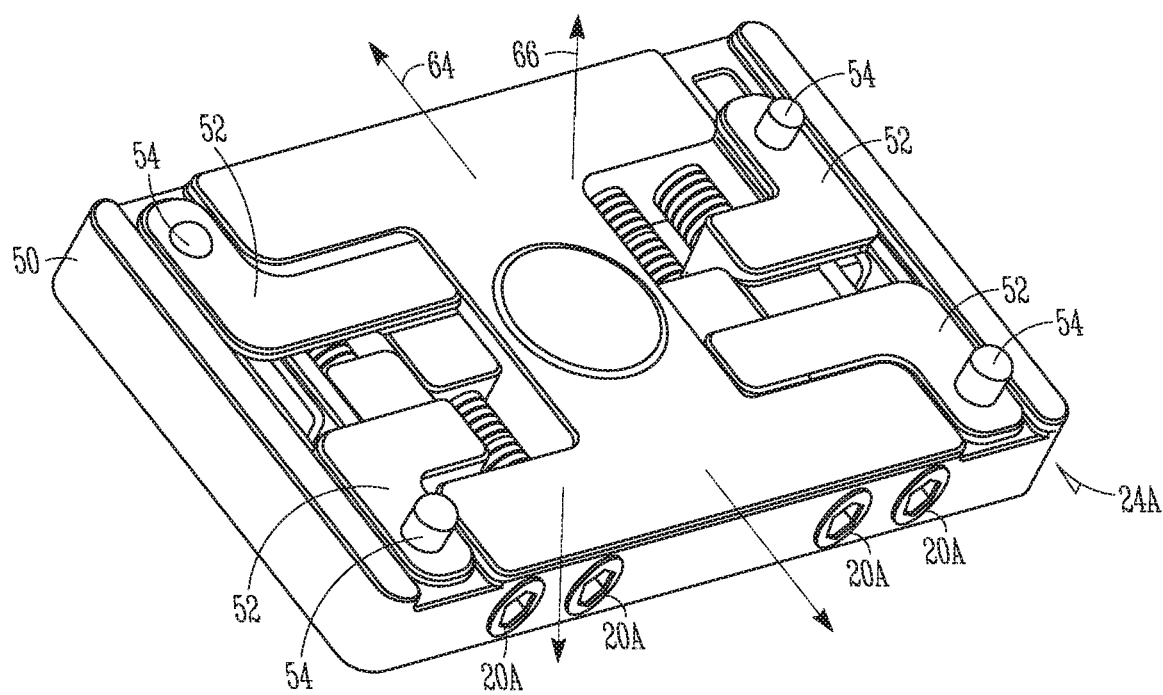
Figure 15:
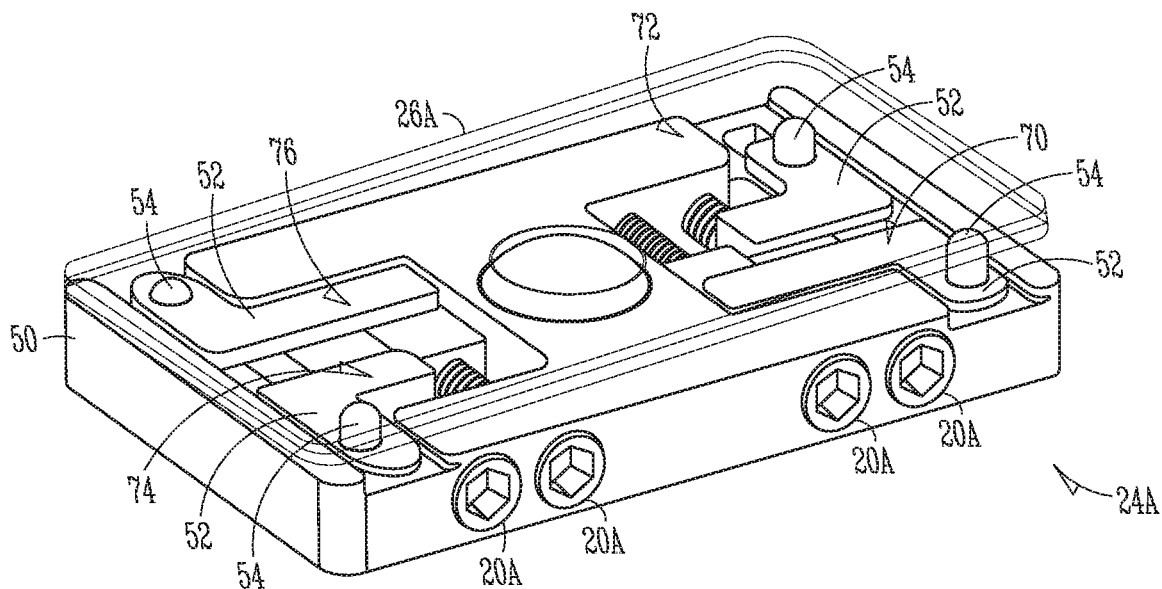

FIGS. 4-15 illustrate alternative examples of an adjustment mechanism for use in knee balancing systems, such as the knee balancing system 10 shown in FIG. 1. More specifically, FIGS. 4-6 illustrate a first alternative example of an adjustment mechanism; FIGS. 7-9 illustrate a second alternative example of an adjustment mechanism; FIGS. 10-12 illustrate a third alternative example of an adjustment mechanism; and FIGS. 13-15 illustrate a fourth alternative example of an adjustment mechanism. Optionally, it is believed that a distal cut guide can be coupled to one or more of these alternative adjustment mechanisms if, for example, an attending surgeon or other caregiver favors soft tissue guided alignment.

Each of the adjustment mechanism alternatives can include, among other things, an adjustable wedge 24A and one or more adjustment screws 20A. The adjustable wedge 24A can include a base member 50, one or more plate members 52, and one or more column members 54. Each base member 50 can include a medial track 56 and a lateral track 57 within which the one or more column members 54 can travel, under the direction of the one or more plate members 52. The medial 56 and lateral 57 tracks can each include one or more actuating ramped surfaces 36A and one or more dead (or neutral) areas 58. When a hidden surface 60 of the one or more column members 54 contacts the one or more actuating ramped surfaces 36A and the one or more dead areas 58, an exposed surface 62 of the column members 54 changes (e.g., increases or decreases) in height and remains fixed at a neutral height, respectively. An increase in height of the exposed surface 62 can cause adjacent portions of a moveable sensor platform 26A to move up relative to (or away from) a main body (see, e.g., the main body 12 of FIG. 1), thereby increasing a collective height of a knee balancing system 10. Conversely, a decrease in height of the exposed surface 62 can cause adjacent portions of the moveable sensor platform 26A to move closer to the main body. A fixing in height of the exposed surface 62, by way of the one or more dead areas 58, can cause adjacent portions of the moveable sensor platform 26A to remain fixed or neutral relative to the main body.

In varying examples, the one or more column members 54 are coupled to the one or more plate members 52 and move when the plate members 52 move. The one or more plate members 52 can be movable within a perimeter of the main body through rotation of the one or more adjustment screws 20A, such as via an adjustment wrench (see, e.g., the adjustment wrench 30 of FIG. 1). In the examples of FIGS. 4-15, movement of the one or more plate members 52 along a substantially horizontal planar direction 64 causes the one or more column members 54 to move or remain fixed along a substantially vertical planar direction 66.

In the example of FIGS. 4-6 (also referred to a dual side, opposing lift example using a single adjustment screw), a base member 50 can include a medial track 56 and a lateral track 57, each track having actuating ramped surfaces 36A and dead areas 58 that are mirror images of one another. Similarly, a hidden surface 60 associated with a medial column member 54 is oriented opposite (or mirror) a hidden surface 60 associated with a lateral column member 54. As a result, movement of a plate member 52 along a substantially horizontal planar direction 64, generated by rotation of a single adjustment screw 20A, causes a height of an exposed surface 62 of one of the medial or lateral column members 54 to change, relative to a main body and along a substantially vertical planar direction 66, while a height of the other column member's exposed surface 62 remains fixed at a neutral height, relative to the main body.

In the example of FIGS. 7-9 (also referred to as a dual side, single lift example using a single adjustment screw), a base member 50 can include identical medial 56 and lateral 57 tracks (i.e., tracks having actuating ramped surfaces 36A and dead areas 58 in identical locations within the base) and identically-oriented medial and lateral column members 54. As a result, movement of a plate member 52 along a substantially horizontal planar direction 64, generated by rotation of a single adjustment screw 20A, causes a height of an exposed surface 62 of each of medial and lateral column members 54 to change or remain fixed at a neutral height, relative to a main body and along a substantially vertical planar direction 66, together.

In the example of FIGS. 10-12 (also referred to as a dual side, dual lift example using two adjustment screws), a base member 50 can include identical medial 56 and lateral 57 tracks (i.e., tracks having actuating ramped surfaces 36A and dead areas 58 in identical locations within the base) and identically-oriented medial and lateral column members 54. However, unlike the example of FIGS. 7-9, this example includes two plate members 52 and two adjustment screws 20A. As a result, a height of an exposed surface 62 of a column member associated with the medial track 56 can be independently adjusted from a height of an exposed surface 62 of a column member associated with the lateral track 57, even though the base member 50 includes identical medial 56 and lateral 57 tracks and the medial and lateral column members 54 are identically-oriented.

In the example of FIGS. 13-15 (also referred to as a quadrant lift example using four adjustment screws), a base member 50 can include identical medial 56 and lateral 57 tracks (i.e., tracks having actuating ramped surfaces 36A and dead areas 58 in identical locations within the base) and identically-oriented medial and lateral column members 54. However, unlike the example of FIGS. 10-12, this example includes two plate members 52 and two adjustment screws 20A associated with each of the medial 56 and lateral 57 tracks. As a result, a height of an exposed surface 62 of a column member 54 associated with each quadrant (e.g., an anterior/medial quadrant 70, a posterior/medial quadrant 72, an anterior/lateral quadrant 74, and a posterior/lateral quadrant 76) of the adjustment mechanism can be independently controlled.

Figure 16:
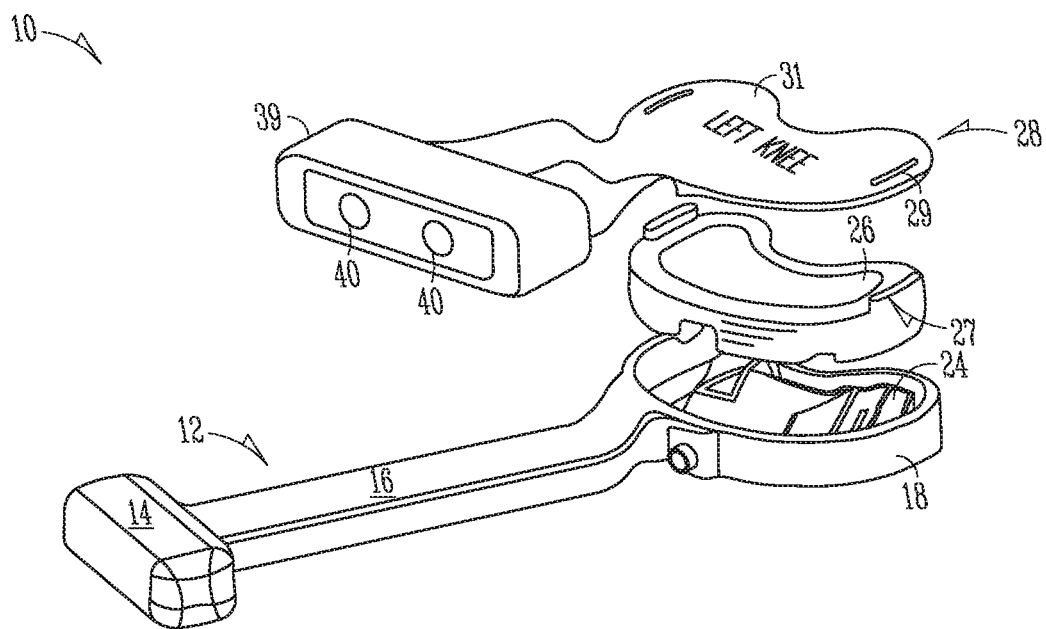
FIG. 16: illustrates an exploded view of a main body coupled with an adjustment mechanism, a movable sensor platform, and a force sensor of a knee balancing system, as constructed in accordance with at least one embodiment.
Figure 17:
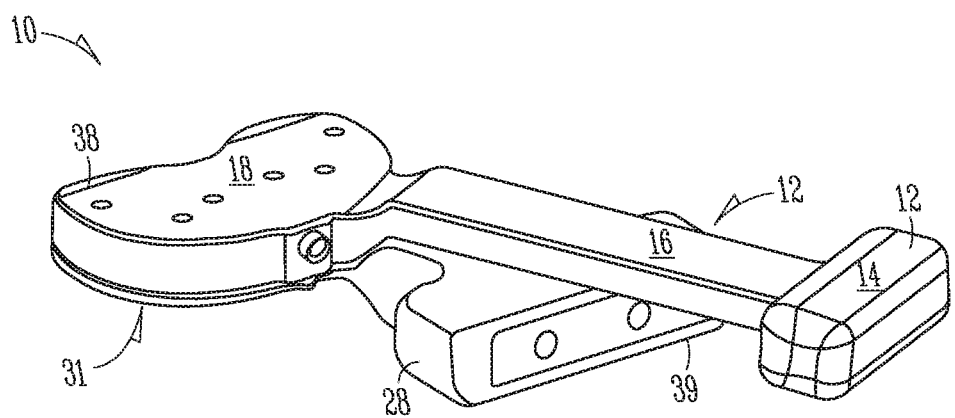
FIG. 17: illustrates an assembled view of a main body, an adjustment mechanism, a movable sensor platform, and a force sensor of a knee balancing system, as constructed in accordance with at least one embodiment.

FIGS. 16 and 17 respectively illustrate exploded and assembled views of a knee balancing system 10, such as the system 10 illustrated in, and described with reference to, FIGS. 1-3. The knee balancing system 10 can include the main body 12, the adjustable wedge 24, the moveable sensor platform 26, and the force sensor 28.

The force sensor 28 can generally include a platform portion 31 and a display portion 39, the latter including indicators 40 to indicate an amount of medial force and an amount of lateral force within a knee joint. Alternatively, the display portions 39 can be separate from the force sensor 28, but communicate with the force sensor 28 through wireless means. The platform portion 31 can include any suitable device for sensing force within the gap formed between the cut distal femur and the cut proximal tibia. For example, the platform portion 31 can include one sensor that is able to sense relative forces applied to medial and lateral sides of the knee joint. The platform portion 31 can include two sensors, one on each of the medial and lateral sides, for sensing force on the medial and lateral aspects of the knee joint.

The display portion 39 can include at least one and typically two indicators 40 to indicate to an attending surgeon or other caregiver an amount (or relative comparison) of force sensed at medial and lateral sides of the knee joint. Since indicators 40 and the numbers displayed can be used for comparison purposes (e.g., an amount of medial force vs. an amount of lateral force), any suitable numbers or indicators can be used that allow the attending surgeon or other caregiver to assess whether the knee is balanced or imbalanced. In the example shown, two LED indicators 40 can each display a number ranging from 0 to 20, representing a comparative amount of sensed force on the medial and lateral sides. If the two displayed numbers are equal, then the sensed forces are balanced. If the numbers are unequal, then the sensed forces are unbalanced. By way of example, but not of limitation, the numbers can equate to about 20 N of force per unit of 1 (for example, the number 2 would indicate 40 N).

The force sensor 28 can include any suitable type of sensor (or sensors), such as but not limited to piezoelectric sensors, force sensing resistors, strain gauges, load cells, other pressure sensors, and other force sensors. In one example, a known voltage is transmitted to sensors, the voltage passing out of sensors is measured, and a percentage of the voltage leaving sensors to the known voltage is calculated. From this percentage, a force can be derived. An analog signal representing the force can be converted to a digital signal with an analog-to-digital (A/D) converter, and the A/D converter can provide the digital signal to a look-up table that determines a display value (or values) representing the force (or forces). An attending surgeon or other caregiver can use the displayed value(s) as an absolute number and/or can move the knee joint and compare force values at flexion and extension. The A/D converter, as well as any additional processing modules for processing the sensed data into usable data, can be housed within the force sensor 28.

The force sensor 28 can be used in a right knee joint, a left knee joint, or both, during any given procedure. The force sensor 28 can be used to measure forces in a first knee joint and simply be flipped over to measure the forces in the opposite knee joint. Alternatively, knee-specific force sensors 28 can be provided.

Referring specifically to FIG. 17, the main body 12 can optionally include a chamfer 38 on its front or anterior aspect. The chamfer 38 can facilitate inserting the system 10 into the gap between a cut distal femur and a cut proximal tibia.

Figure 18:
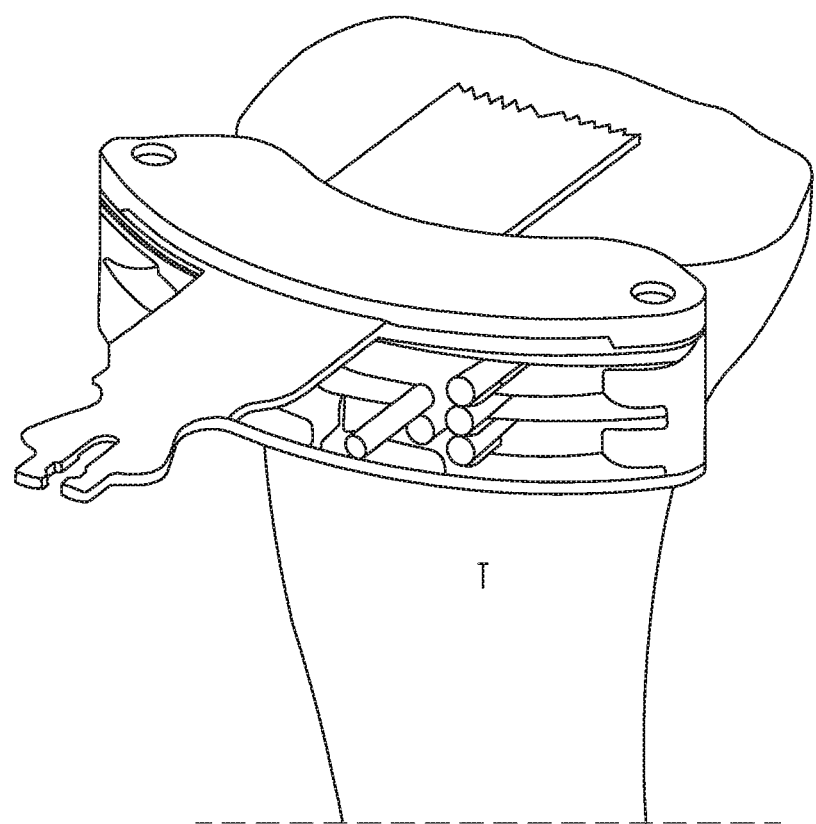
FIG. 18: illustrates a perspective view of cutting a proximal end of a tibia, as constructed in accordance with at least one embodiment.
Figure 19:
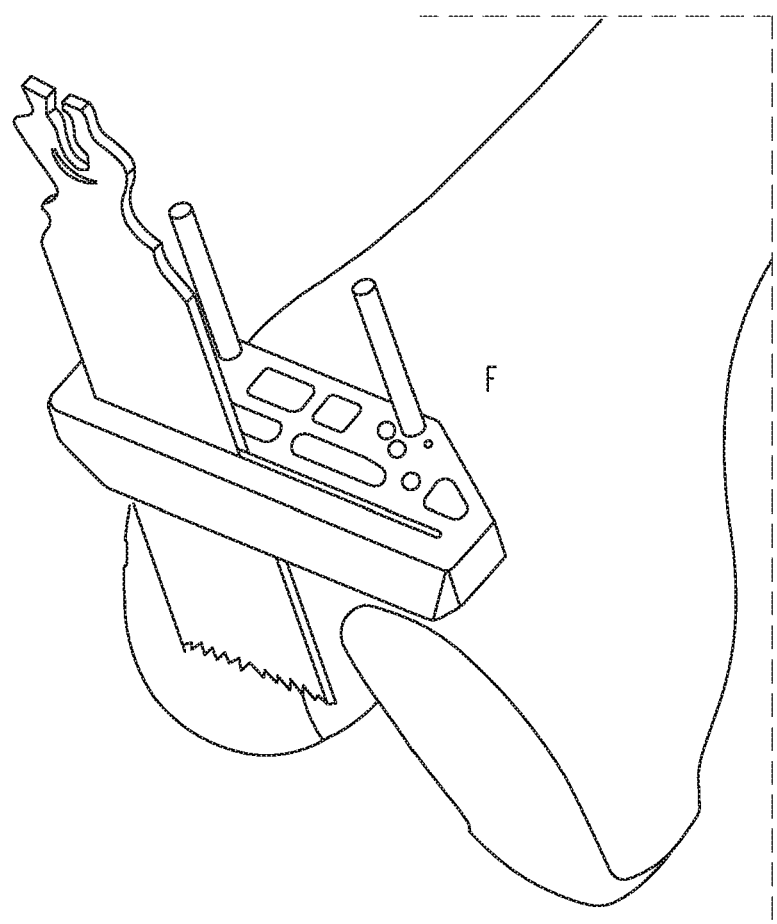
FIG. 19: illustrates a perspective view of cutting a distal end of a femur, as constructed in accordance with at least one embodiment.
Figure 20:
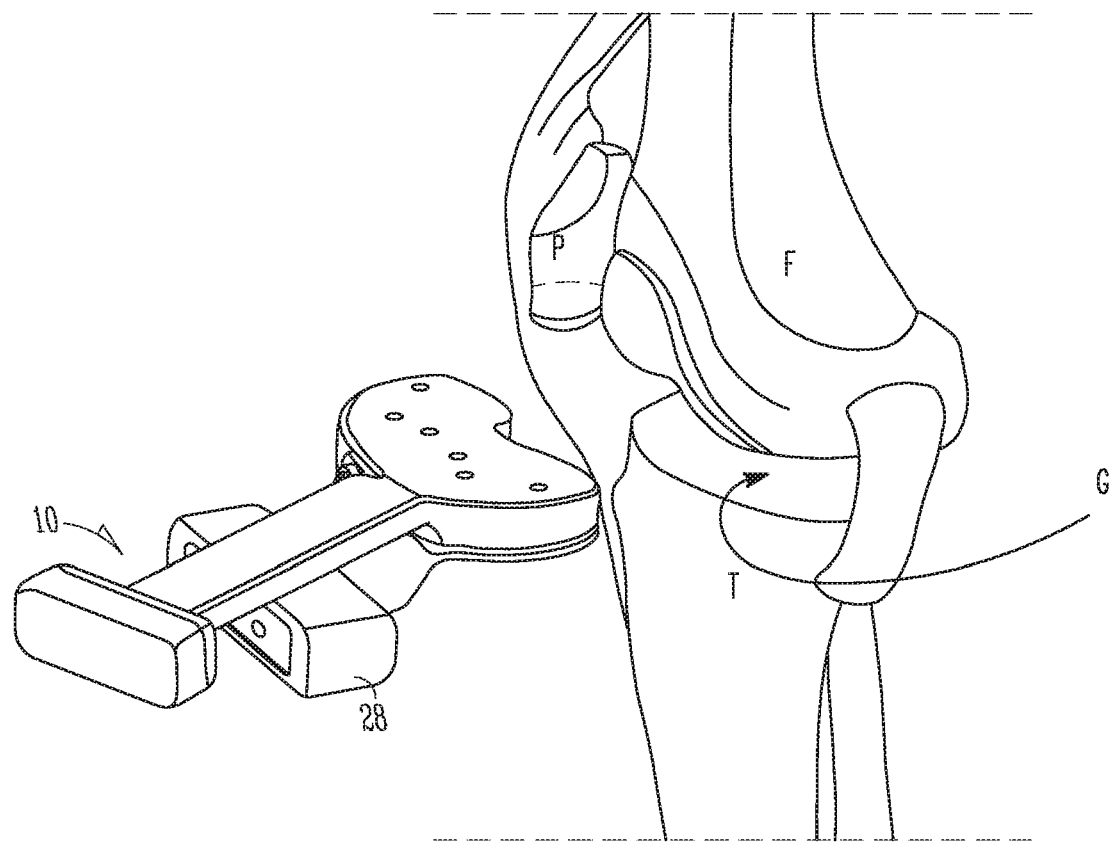
FIG. 20: illustrates a perspective view of inserting a knee balancing system into a gap formed between a cut surface on a distal end of a femur and a cut surface on a proximal end of a tibia, as constructed in accordance with at least one embodiment.

FIGS. 18-24 pictorially illustrate a method for balancing a knee joint during a knee surgical procedure. As shown in FIGS. 18 and 19, cuts can be made to a proximal tibia T and a distal femur F using any suitable bone cutting technique(s). These cuts create a gap G between the two opposing bone knee joint surfaces. As shown in FIG. 20, a patella P can be moved aside and a knee balancing system 10 can inserted, in its collapsed ("thin") configuration, into the gap G between the cut distal femur F and the cut proximal tibia T.

Figure 21:
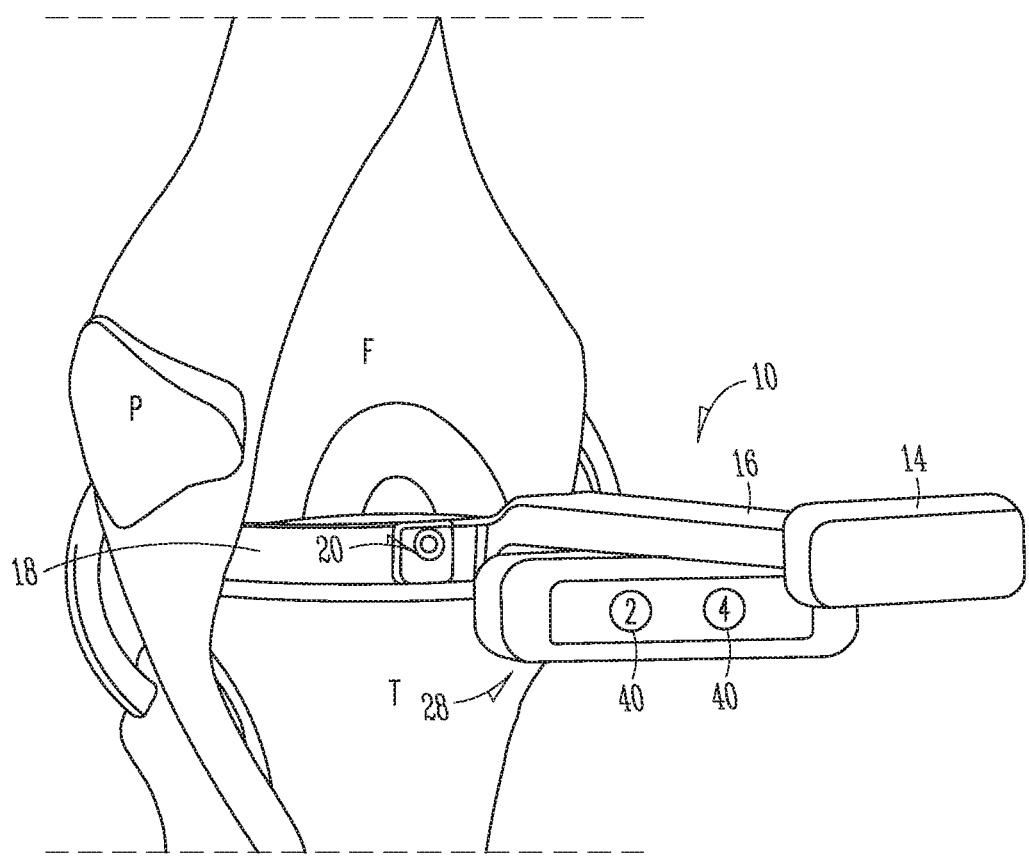
FIG. 21: illustrates a perspective view of a knee balancing system positioned within a gap formed between a cut surface on a distal end of a femur and a cut surface on a proximal end of a tibia, as constructed in accordance with at least one embodiment.

FIG. 21 illustrates a front view of the knee joint, with the system 10 in place within the gap G and before any adjustment has been made to expand the system 10 to increase its collective height. As is evident from this figure and as discussed above, the shaft 16 and the handle 14 of the main body 12 can be offset relative to a center of the platform 18. This offset configuration can allow for easier access to the front of the knee joint for adjustment via the adjustment screw 20. In the example shown, sensed forces on the medial and lateral aspects of the knee joint are currently out of balance and are at a low end of the possible numerical range, as designated by the displayed numbers of 2 and 4, since no height adjustment has been made.

Figure 22:
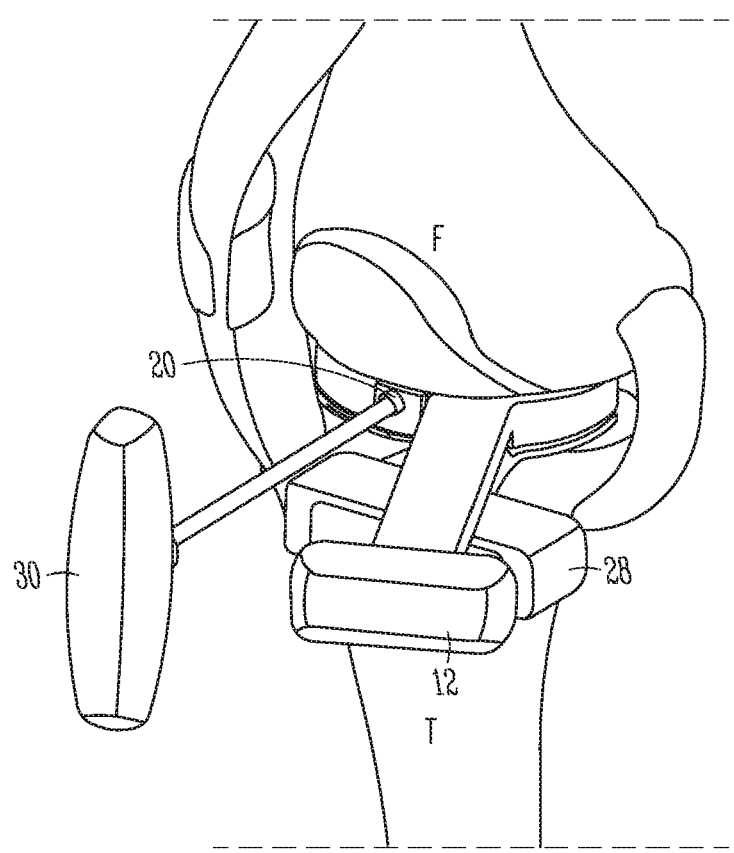
FIG. 22: illustrates an elevation perspective view of adjusting an adjustment mechanism of a knee balancing system to increase or decrease a collective height of the system, as constructed in accordance with at least one embodiment.
Figure 23A:
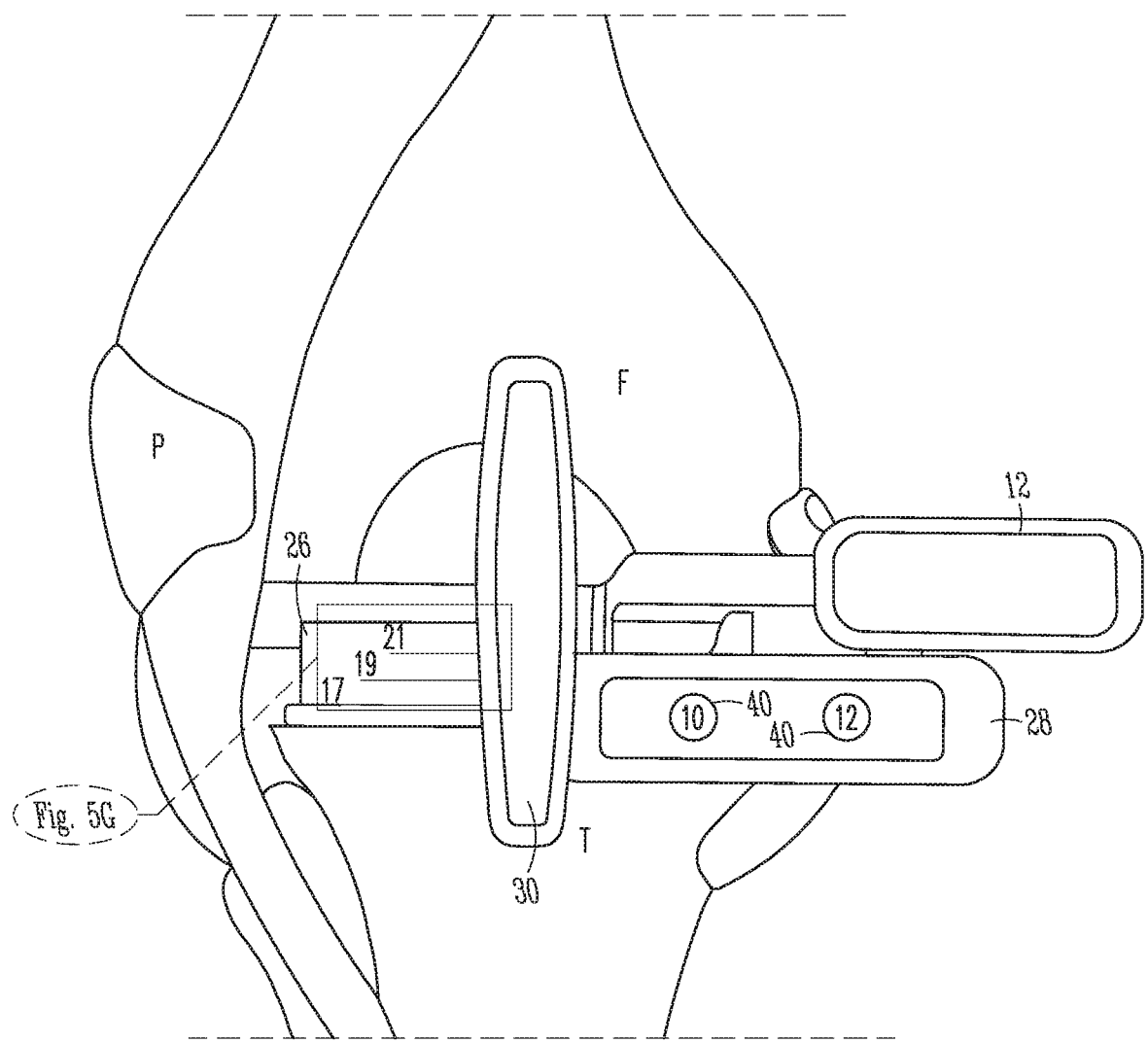
FIG. 23A: illustrates a front perspective view of adjusting an adjustable mechanism of a knee balancing system to increase or decrease a collective height of the system, as constructed in accordance with at least one embodiment.
Figure 23B:
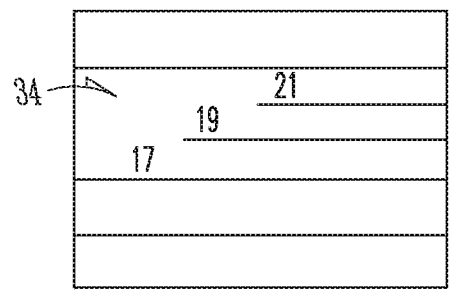
FIG. 23B: illustrates a close-up view of a plurality of distraction height markings of a moveable sensor platform, included in a knee balancing system, as constructed in accordance with at least one embodiment.

FIG. 22 illustrates a perspective view of the knee joint, with the adjustment wrench 30 being used to adjust the system's 10 collective height. After the system 10 is inserted into the knee gap, the adjustment wrench 30 can be used to expand the system's 10 height. In various alternative examples, any suitable adjustment members can be used in place of the adjustment wrench 30, the adjustment screw 20, the adjustment screw capture nut 22 (FIG. 1), and the adjustable wedge 24 (FIG. 1). For example, a screwdriver, a key, a removable dial, a pump with an air bladder, or any of a number of suitable devices can be used for adjusting the collective height of the portions of the system 10 within the knee joint gap G.

FIGS. 23A and 23B again illustrate a front view of the knee joint; this time after the system 10 has been adjusted to increase its collective height. Graduated distraction markings 34 on an outer surface of the moveable sensor platform 26 are now visible, indicating an approximate measurement of the gap G between the cut distal femur F and the cut proximal tibia T (in the example shown, about 21 millimeters). Sensed force has increased on both sides of the knee, relative to FIG. 21, as indicated by the indicator 40 displaying the larger numbers 10 and 12. Typically, the system 10 is adjusted by an attending surgeon or other caregiver until he/she believes that soft tissues around the knee are activated, so that if ligament release(s) is performed, it will affect the numbers displayed on the indicator 40. Alternatively, the attending surgeon or other caregiver can increase the height of the system 10 until a desired reading of force measurement is indicated on the indicator 40.

Figure 24:
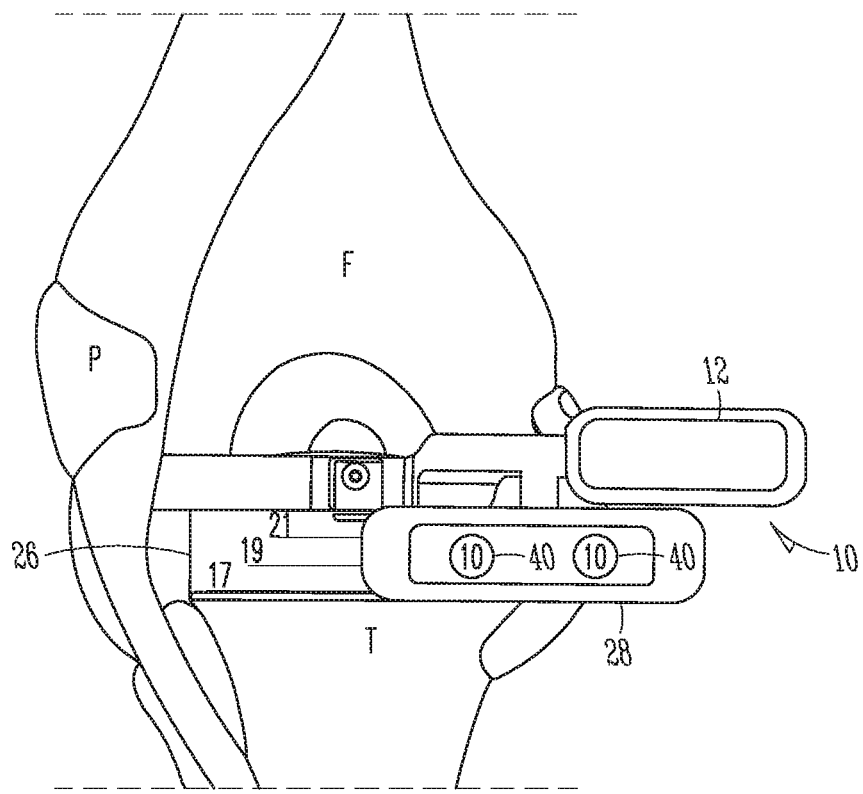
FIG. 24: illustrates a front perspective view of a knee balancing system after ligament release(s) has been performed to balance the medial and lateral forces imposed on the system, as constructed in accordance with at least one embodiment.

FIG. 24 illustrates a front view of the knee joint after ligament release(s) has been performed to balance medial and lateral forces imposed on the system 10. Ligaments can be released on one or both sides of the knee joint to balance tension about the joint and thus the forces sensed by the force sensor 28. The balanced forces are indicated by indicator 40 numerical readings of 10 and 10 on both medial and lateral sides. Now that ligament balancing has been achieved, the system 10 can be removed from the knee joint and the rest of the knee replacement surgical procedure can be performed. In some examples, the system 10 can subsequently be used on the opposite knee.

Closing Notes

Devices, systems and methods are provided for facilitating knee balancing during a knee replacement surgery. A system can include a force sensor, a main body, a moveable sensor platform, and an adjustment mechanism. The force sensor can sense one or more forces applied within a knee joint, including forces applied on a medial side and a lateral side. The movable sensor platform can be coupled between the force sensor and the main body. The adjustment mechanism can adjust the moveable sensor platform, relative to the main body, thereby adjusting a height of the system. A method can include inserting portions of a knee balancing system into a gap formed between a distal end of a femur and a proximal end of a tibia, adjusting an adjustable mechanism of the knee balancing system to increase or decrease a collective height of the system, and sensing and displaying the medial and lateral forces.

The above Detailed Description includes references to the accompanying drawings, which form a part of the Detailed Description. The drawings show, by way of illustration, specific embodiments in which the present knee balancing devices, systems and methods can be practiced. These embodiments are also referred to herein as "examples." While certain examples are shown and described with respect to a specific knee (i.e., a left knee or a right knee), it is to be appreciated that the present disclosure is equally applicable to both the left and right knees. All examples can also be configured and used in partial or total knee replacement procedures. It is believed that similar examples can be used with other non-knee areas of orthopedics, which can benefit through distraction from a thin profile, such as but not limited to total disc arthroplasty.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "anterior" or "front" refers to a direction generally toward the front of a patient, "posterior" or "back" refers to a direction generally toward the back of the patient, "medial" refers to a direction generally toward the middle of the patient, and "lateral" refers to a direction generally toward the side of the patient. In this document, "bottom side" refers to a side of a knee balancing system that faces a proximal tibial surface and "top side" refers to a side of a knee balancing system that faces a distal femoral surface. Notably, the present inventors appreciate that the present knee balancing devices, systems and methods can be configured such that a bottom side in a first embodiment of a knee balancing system can be a top side in a second embodiment of the knee balancing system; similarly, a top side in the first embodiment can be a bottom side in the second embodiment. As such, reference to a bottom side, a top side, or similar should not be viewed as limiting.

In the appended claims, the terms "including" and "in which" are used as the plain-English equivalents of the respective terms "comprising" and "wherein." The terms "including" and "comprising" are open-ended, that is, a system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A distraction device for balancing a knee, the distraction device comprising:
   a base member;
   a moveable platform positioned on a superior surface of the base member;
   a medial adjustment portion including a linear medial track and a medial adjustment input; and a lateral adjustment portion including a linear lateral track and a lateral adjustment input;

wherein each of the linear medial track and the linear lateral track are recessed within the base member and include one or more actuating ramped surfaces in fixed locations along each respective track.

2. The device of claim 1, wherein the medial adjustment input includes a medial screw or medial bolt, and the lateral adjustment input includes a lateral screw or lateral bolt.

3. The device of claim 2, wherein the medial adjustment portion includes a medial plate member and a medial column member, and wherein the lateral adjustment portion includes a lateral plate member and a lateral column member.

4. The device of claim 3, wherein the medial plate member is moveable relative to the base member through rotation of the medial screw or the medial bolt, and the lateral plate member moveable relative to the base member through rotation of the lateral screw or the lateral bolt.

5. The device of claim 4, wherein the medial column member moves along a vertical linear direction in response to movement of the medial plate member along a horizontal linear direction, which is perpendicular to the vertical linear direction.

6. The device of claim 5, wherein the lateral column member moves along the vertical linear direction in response to movement of the lateral plate member along the horizontal linear direction which is perpendicular to the vertical linear direction.

7. The device of claim 6, wherein the medial column member moves independent of the lateral column member.

8. The device of claim 5, wherein the medial column member travels within the linear medial track to engage a ramp surface of the one or more actuating ramped surfaces within the linear medial track, and the lateral column member travels within the linear lateral track to engage a ramp surface of the one or more actuating ramped surfaces within the linear lateral track.

9. A method for adjusting a moveable platform of a knee balancing system, the method comprising:
providing components of the knee balancing system, including a main body and a moveable sensor platform positioned in relation to the main body to move responsive to an adjustment mechanism positioned within the main body;
adjusting the adjustable mechanism to cause sliding engagement between one or more column elements and one or more actuating ramped surfaces in fixed locations within a linear medial track and a linear lateral track each track recessed within a base member within the adjustable mechanism to produce an increase or decrease in height of the moveable sensor platform relative to the main body, the increase or decrease in height occurring on a medial side of the moveable sensor platform or a lateral side of the moveable sensor platform.

10. The method of claim 9, further comprising:
engaging a first screw or first bolt of the adjustment mechanism with an adjustment instrument; and
turning the adjustment instrument a first direction to increase a medial height of the system.

11. The method of claim 10, wherein turning the adjustment instrument in a second direction decreases the medial height of the system.

12. The method of claim 10, wherein turning the adjustment instrument in the first direction moves a first plate in a first linear direction.

13. The method of claim 12, wherein movement of the first plate in the first linear direction causes a first column member to engage a first actuating ramped surface of the one or more actuation ramped surfaces within the linear medial track.

14. The method of claim 10, further comprising:
after engaging the first screw or first bolt of the adjustment mechanism with the adjustment instrument, engaging a second screw or second bolt of the adjustment mechanism with the adjustment instrument; and
after engaging the second screw or the second bolt of the adjustment mechanism with an adjustment instrument, turning the adjustment instrument a first direction to increase a lateral height of the system.

15. The method of claim 14, wherein after engaging the second screw or the second bolt of the adjustment mechanism with the adjustment instrument, turning the adjustment instrument in a second direction to decrease the lateral height of the system.

16. The method of claim 14, wherein after engaging the second screw or the second bolt of the adjustment mechanism with an adjustment instrument, turning the adjustment instrument in the first direction moves a second plate in a first linear direction.

17. The method of claim 16, wherein movement of the second plate in the first linear direction causes a second column member to engage a second actuating ramped surface of the one or more actuation ramped surfaces within the linear lateral track.

18. An adjustment system for balancing a knee comprising:
a main body;
a moveable platform positioned on a superior surface of the main body; and
an adjustment mechanism configured to adjust the moveable platform relative to the main body, the adjustment mechanism positioned within the main body and comprising:
a medial adjustment portion including a linear medial track and a medial adjustment input; and
a lateral adjustment portion including a linear lateral track and a lateral adjustment input;
wherein each of the linear medial track and the linear lateral track are recessed within the main body and include one or more actuating ramped surfaces in fixed locations along each respective track.

19. The system of claim 18, wherein the medial adjustment input includes a medial screw or medial bolt, and the lateral adjustment input includes a lateral screw or lateral bolt.

20. The system of claim 19 wherein an adjustment mechanism engages a first screw or first bolt to increase or decrease a medial height of the moveable platform, and after the adjustment mechanism engages the first screw or first bolt to increase or decrease the medial height, the adjustment instrument mechanism engages the second screw to increase or decrease a lateral height of the moveable platform.

* * * * *